United States Patent [19]
Tang et al.

[11] Patent Number: 5,891,917
[45] Date of Patent: Apr. 6, 1999

[54] CERTAIN ACRYLONITRILE-SULFONAMIDE DERIVATIVES

[75] Inventors: Peng Cho Tang, Moraga; Li Sun, Foster City; Asaad S. Nematalla, Walnut Creek; Gerald McMahon, San Francisco, all of Calif.

[73] Assignee: Sugen, Inc., Redwood City, Calif.

[21] Appl. No.: 957,260

[22] Filed: Oct. 24, 1997

Related U.S. Application Data

[63] Continuation of Ser. No. 480,275, Jun. 7, 1995, abandoned.
[51] Int. Cl.$^6$ ..................... C07C 255/08; C07C 255/32; A61K 31/18
[52] U.S. Cl. ..................... 514/604; 558/390; 546/298; 549/80
[58] Field of Search ........................ 558/390; 514/604

[56] References Cited

U.S. PATENT DOCUMENTS

| | | | |
|---|---|---|---|
| 4,966,849 | 10/1990 | Vallee et al. | 435/199 |
| 5,217,999 | 6/1993 | Levitzki et al. | 514/613 |
| 5,302,606 | 4/1994 | Spada et al. | 514/357 |
| 5,330,992 | 7/1994 | Eissenstat et al. | 514/312 |

FOREIGN PATENT DOCUMENTS

| | | |
|---|---|---|
| 566 266 | 10/1993 | European Pat. Off. . |
| WO 91/15495 | 10/1991 | WIPO . |
| WO 92/20642 | 11/1992 | WIPO . |
| WO 92/21660 | 12/1992 | WIPO . |
| WO 94/03427 | 2/1994 | WIPO . |
| WO 94/10202 | 5/1994 | WIPO . |
| WO 94/14808 | 7/1994 | WIPO . |

OTHER PUBLICATIONS

Aaronson, S.A. (1991). Growth factors and cancer Science 254, 1146–1153.

Arvidsson, A.–K., et al. (1994). Tyr–716 in the platelet–derived growth factor b–receptor kinase insert is involved in GRB2 binding and ras activation. Molecular and Cellular Biology 14, 6715–6726.

Baserga, R. (1995). The insulin–like growth factor I receptor: a key to tumor growth? Cancer Research 55, 249–252.

Bisbee, C. (1995). Scatter factor/hepatocyte growth factor gene deletion leads to death in knockout mice. BioWorld Today 24 Feb. 1995, 2.

Carraway, L. K., et al. (1994). Ther erbB3 Gene Product Is a Receptor for Heregulin. The Journal of Biological Chemistry 269, 14303–14306.

Carraway, K. L., and Cantley, L. C. (1994). A Neu Acquaintance for ErbB3 and ErbB4: A role for receptor heterodimerization in growth signaling. Cell 78, 5–8.

Claesson–Welsh, L. (1994). Signal transduction by the PDGF receptors. Progress in Growth Factor Research 5, 37–54.

Cullen, K. J., Yee, D., and Rosen, N. (1991). Insulinlike Growth Factors in Human Malignancy. Cancer Investigation 9, 443–454.

Dati, C., Antoniotti, S., Taverna, D., Perroteau, I., and De Bortoli, M. (1990). Inhibition of c–erB–2 oncogene expression by estrogens in human breast cancer cells. Oncogene 5, 1001–1006.

Decker, T., and Lohmann–Matthes, M.–L. (1988). A quick and simple method for quantitation of lactate dehydrogenase release in measurements of cellular cytotoxicity and tumor necrosis factor (TNF) activity. J. of Imm. Methods 15, 61–69.

de Vries, C., Escobedo, J.A., Ueno, H., Houck, K., Ferrara, N., and Williams, L.T. (1992). The fms–like tyrosine kinase, a receptor for vascular endothelial growth factor. Science 255, 989–991.

Dougall, W.C., Qian, X., Peterson, N.C., Miller, M. J., Samanta, A., and Greene, M. I. (1994). The neu–oncogene: signal transduction pathways, transformation mechanisms and evolving therapies. Oncogene 9, 2109–2123.

Fendly, B.M. (1990). Characterization of murine monoclonal antibodies reactive to either the human epidermal growth factor receptor or HER2/neu gene product. Cancer Research 50, 1550–1558.

Ferrara, N., and ⊢ enzel, W. J. (1989). Pituitary follicular cells secrete a novel hepair–binding growth factor specific for vascular endothelial cells. Biochemical and Biophysical Research Communications 161, 851–858.

Fingl, E., and Woodbury, D.M. (1975). The Pharmacological Basis of Therapeutics Chapter I, 1–46.

Floege, J., Eng, E., Young, B. A., and Johnson, R. J. (1993). Factors involved in the regulation of mesangial cell proliferation in vitro and in vivo. Kidney International 43, S–47–S–54.

Folkman, J. (1971. Tumor Angiogenesis: therapeutic implications. The New England Journal of Medicine v. 285, 18 Nov. 1971, 1182–1186.

Folkman, J. (1990). What is the evidence that tumors are angiogenesis dependent? Journal of the National Cancer Institute 82, 4–6.

Folkman, J., and Shing, Y. (1992). Angiogenesis. The Journal of Biological Chemistry 267, 10931–10934.

Fry, M. J., Panayotou, G., Booker, G. W., and Waterfield, M.D. (1993). New insights into protein–tyrosine kinase receptor signaling complexes. Protein Science 2, 1785–1797.

Giordano, S., Di Renzo, M. F., Olivero, M., Mondino, A., Zhen, Z., Medico, E., and Comoglio, P.M. (1992). The c–met/HGF receptor in human tumours. European Journal of Cancer Prevention 1, 45–49.

Gottardis, M.M., Robinson, S.P., and Jordan, C.V. (1988). Estradiol–stimulated growth of MCF–7 tumors implanted in athymic mice: A model to study the tumoristatic action of tamoxifen. J. Steriod Biochem. 30, 311–314.

(List continued on next page.)

Primary Examiner—Alan L. Rotman
Attorney, Agent, or Firm—Lyon & Lyon LLP

[57] ABSTRACT

The present invention relates to molecules capable of modulating tyrosine signal transduction to prevent and treat cell proliferative disorders or cell differentiation disorders associated with particular tyrosine kinases by inhibiting one or more abnormal tyrosine kinase activities.

16 Claims, No Drawings

OTHER PUBLICATIONS

Harris, J.R., Lippman, M. E., Veronesi, U., and Willett, W. (1992). Breast Cancer. New England Journal of Medicine 327, 319–328.

Honegger, A.M., et al. (1987). Point mutation at the ATP binding site of EGF receptor abolishes protein–tyrosine kinase activity and alters cellular routing. Cell 51, 199–209.

Houck, K. A., et al. (1992). Dual regulataion of vascular endothelial growth factor bioavailability by genetic and proteolytic mechanisms. The Journal of Biological Chemisstry 267, 26031–26037.

Hu, P., et al. (1992). Interaction of Phosphatidylinositol 3–Kinase–Associated p85 with Epidermal Growth Factor and Platelet–Derive Growth Factor Receptors. Molecular and Cellular Biology 12, 981–990.

Jellinek, D., Green, L. S., and Janjic, N. (1994). Inhibition of receptor binding by high–affinity RNA ligands to vascular endothelial growth factor. Biochemistry 33, 10450–10456.

Jücker, M., et al. (1994). The Met/Hepatocyte Growth Factor Receptor (HGFR) Gene is Ovexpressed in Some Cases of Human Leukemia and Lymphoma. Leukemia Research 18, 7–16.

Kashishian, A., Kazlauskas, A., and Cooper, J.A. (1992). Phosphorylation sites in the PDGF receptor with different specificities for binding GAP and P13 kinase in vivo. The EMBO J 11, 1373–1382.

Kashishian, A., and Cooper, J. A. (1993). Phosphorylation sites at the C–terminus of the platelet–derived growth factor receptor bind phospholipase Cg1. Molecular Biology of the Cell 4, 49–57.

Kazlauskas, A., et al. (1993). The 64–kDa protein that associates with the platelet–derived growth factor receptor b subunit via Tyr–1009 is the SH2–containing phosphotyrosine phosphatase Syp. Proc. Natl. Acad. Sci. USA 90, 6939–6942.

Kendall, R.L., and Thomas, K. A. (1993). Inhibition of vascular endothelial cell growth factor activity by an endogenously encoded soluble receptor. Proc. Natl. Acad. Sci. 90, 10705–10709.

Kim, K. J., Li, B., Winer, J., Armanini, M., Gillett, N., Phillips, H.S., and Ferrara, N. (1993). Inhibition of vascular endothelial growth factor–induced angiogenesis suppresses tumour growth in vivo. Nature 362, 841–844.

Kinsella, J.L., Grant, D.S., Weeks, B. S., and Kleinman, H.K. (1992). Protein kinase C regulates endothelial cell tube formation on basement membrane matrix, matrigel. Experimental Cell Research 199, 56–62.

Klagsbrun, M., and Soker, S. (1993). VEGF/VPF: the angiogenesis factor found? Current Biology 3, 699–702.

Korzseniewski, C., and Callewaert, D.M. (1993). An enzyme–release assay for natural cytotoxicity. Journal of Immunological Methods 64, 313–320.

Skehan, P., et al. (1990). New Colorimetric cytotoxicity assay for anticancer–drug screening. Journal of the National Cancer Institute 82, 1107–1112.

Slamon, D. J., Clark, G. M., Wong, S. G., Levin, W.J., Ullrich, A., and McGuire, W. L. (1987). Human Breast Cancer: Correlation of Relapse and Survival with Amplification of the HER–2/neu Oncogene. Science 235, 177–182.

Slamon, D.J., et al. (1989). Studies of the HER–2/neu Proto–oncogene in Human Breast and Ovarian Cancer. Science 244, 707–712.

Sliwkowski, M. X., et al. (1994). Coexpression of erbB2 and erbB3 Proteins Reconstitutes a High affinity receptor for Heregulin. The Journal of Biological Chemistry 269, 14661–14665.

Soman, N. R., Correa, P., Ruiz, B. A., and Wogan, G.N. (1991). The TPR–MET oncogenic rearrangement is present and expressed in human gastric carcinoma and precursor lesions. Proc. Natl. Acad. Sci. USA 88, 4892–4896.

Stein, D., et al. (1994). The SH2 domain protein GRB–7 is co–amplified, overexpressed and in a tight complex with hER2 in breast cancer. EMBO 13, 1331–1340.

Suzuki, K., et al. (1994). Expression of the c–met protoonocogene in human hepatocellular carcinoma. Hepatology, 1231–1236.

Takano, S. Gately, S., Jiang, J. B., and Brem, S. (1993). Inhibition of angiogenesis by a novel diaminoanthraquinone that inhibits protein kinase C. Mol. Bio. of the Cell 4, 358A.

Twamley–Stein, G., et al. (1993). The Src family tyrosine kinases are required for platelet–derived growth factor–mediated signal transduction in NIH 3T3 cells. Proc. Natl. Acad. Sci. USA 90, 7696–7700.

Ullrich, A., and Schlessinger, J. (1990). Signal transduction by receptor with tyrosine kinase activity. Cell 61, 203–212.

Vaisman, N., Gospodarowicz, D., and Neufeld, G. (1990). Characterization of the receptors for vascular endothelial growth factor. The Journal of Biological Chemistry 265, 19461–19466.

Wada, T., et al. (1990). Anti–receptor antibodies reverse the phenotype of cells transformed by twointeracting proto–oncogene encoded receptor proteins. Oncogene 5, 489–495.

Wada, T., et al. (1990). Intermolecular association of the p185neu protein and EGF receptor modulates EGF receptor function. Cell 61, 1339–1347.

Wärri, A.M., et al. (1991). Estrogen suppression of erbB2 expression is associated with increased growth rate of ZR–75–1 human breast cancer cells in vitro and in nude mice. Int. J. Cancer 49, 616–623.

Weidner, N., Semple, J.P., Welch, W. R., and Folkman, J. (1991). Tumor angiogenesis and metastasis—correlation in invasive breast carcinoma. The New England Journal of Medicine 324,1–7.

Weidner, K.M., et al. (1993). Molecular characteristics of HFG–SF and its role in cell motility and invasion. Hepacyte Growth Factor (HFG–SF and its role in cell motillity and invasion. Hepacyte Growth Factor–Scatter Factor (HGF–SF) and the C–Met Receptor, 311–328.

Wright, P.S., Cross–Doersen, D., Miller, J. A., Jones, W. D., and Bitonit, A. J. (1992). Inhibition of angiogenesis in vitro and in ovo with an inhibitor of cellular protein kinases, MDL 27032. Journal of Cellular Physiology 152, 448–457.

Yarden, Y., and Ullrich, A. (1988). Growth factor receptor tyrosine kinases. Ann. Rev. Biochem. 57, 443–478.

Sammes, M. P., Wylie, C. M., and Hoggett, J. G. (1971). a–cyano–sulphonyl chlorides: their preparation and reactions with amines, alcohols, and Enamines. J. Chem Soc., 2151–2155.

Krywicki, and Yee, D. (1992). The insulin–like growth factor family of ligands, receptors, and binding proteins. Breast Cancer Research and Treatment 22, 7–19.

Mariani, M., et al. (1994). Inhibition of angiogenesis by PCE26806, a potent tyrosine kinase inhibitor. Proceedings of the American Association for Cancer Research 35, 381.

Marshall, E. (1993). Search for a killer:focus shifts from fat to hormones. Science 259, 618–621.

Millauer, B., et al. (1993). High Affinity VEGF Binding and Developmental Expression Suggest FLK–1 as a Major Regulator of Vasculogenesis and Angiogenesis. Cell 72, 835–846.

Mosmann, T. (1981). Rapid Colorimetric assay for cellular growth and survival: application to proliferation and cytotoxicity assays. Journal of Immunological Methods 65, 55–63.

Natali, P. G., et al. (1993). Expression of the C–Met/HGF receptor in human melanocytic neoplasms: demonstration of the relationship to malignant melanoma tumour progression. Br. J. Cancer 68, 746–750.

Nishimura, R., et al. (1993). Two Signaling Molecules Share a Phosphotyrosine–Containing Binding Site in the Platelet–Derived Growth Factor Receptor. Molecular and Cellular Biology 13, 889–6896.

Osborne, C. K., Hobbs, K., and Clark, G. M. (1985). Effect of estrogens and antiesrogens on growth of human breast cancer cells in athymic nude mice. Cancer Research 45, 584–590.

Ozzello, L., and Sordat, M. (1980). Behavior of tumors produced by transplantation of human mammary cell lines in athymic nude mice. Europ. J. Cancer 16, 553–559.

Plowman, G. D., Green, J. M., Rothwell V. M., and Buckley, S. (1993). Heregulin induces tyrosine phosphorylation of HER4/p180erbB4. Nature 366, 473–475.

Quinn, T.P., et al. (1993). Fetal liver kinase 1 is a receptor for vascular endothelial growth factor and is selectively expressed in vascular endothelium. Proc. Natl. Acad. Sci. USA 90, 7533–7537.

Di Renzo, M. F., Narsimhan, R. P., Olivero, M., Bretti, S., Giordano, S., Medico, E., Gaglia, P., Zara, P., and Comoglio, P. M. (1991). Expression of the Met/HGF receptor in normal and neoplastic human tissues. Oncogene 6, 1997–2003.

Di Renzo, M. F., Poulsom, R., Olivero, M., Comoglio, P. M., and Lemoine, N. R. (1995). Expression of the Met/Hepatocyte growth factor receptor in human pancreatic cancer. Cancer Research 55, 1129–1138.

Rozakis–Adcock, M., et al. (1992). Association of the Shc and Grb2/Sem5 SH2–containing proteins is implicated in activation of the Ras pathway by tyrosine kinases. Nature 360, 689.

Rygaard, J., and Poulson, C. O. (1969). Heterotransplantation of a human malignant tumour to "nude" mice. Acta. path. microbiol scand. 77, 758–760.

Samanta, A., LeVea, C.M., Dougall, W. C., Qian, X., and Greene, M. I. (1994). Ligand and p185c–neu density govern receptor interactions and tyrosine kinase activation. Proc. Natl. Acad. Sci. 91, 1711–1715.

Schlessinger, J., and Ullrich, A. (1992). Growth factor signaling by receptor tyrosine kinases. Neuron 9, 383–391.

Schlessinger, J. (1988). Signal transduction by allosteric receptor oligomerization. TIBS 13, 443–447.

Schmid, C. (1993). IGFs: function and clinical importance 2 The regulation of osteoblast function by hormones and cytokines with special reference to insulin–like growth factors and their binding proteins. J. of Int. Med. 234, 535–542.

Schuchter, L. M., Esa, A. H., May, W. S., Laulis, M. K., Pettit, G. R., and Hess, A. D. (1991). Successful treatment of murine melanoma with bryostaatin 1. Cancer Research 51, 682–687.

Scott, G. K., et al. (1991). p185HER2 Signal Transduction in breast cancer cells. The Journal of Biological Chemistry 266, 14300–14305.

Seibert, K., Shafie, S. M., Triche, T. J., Whang–Peng, J. J., O'Brien, S. J., Toney, J. H., Huff, K. K., and Lippman, M. E. (1983). Clonal variation of MCF–7 breast cancer cells in vitro and in athymic nude mice. Cancer Research 43, 2223–2239.

Shafie, S. M., and Grantham, F. H. (1981). Role of hormones in the growth and regression of human breast cancer cells (MCF–7) transplanted into athymic nude mice. JNCI 67, 51–56.

Shibuya, M., et al. (1990). Nucleotide sequence and expression of a novel human receptor–type tyrosine kinase gene (flt) closely related to the fms family. Oncogene 5, 519–524.

CERTAIN ACRYLONITRILE-SULFONAMIDE DERIVATIVES

This is a continuation of application Ser. No. 08/480,475, filed Jun. 7, 1995, abandoned.

FIELD OF THE INVENTION

The present invention relates generally to the field of tyrosine kinase inhibition. More specifically, the present invention relates to the use of small organic molecules to prevent and treat cell proliferative disorders or cell differentiation disorders associated with particular tyrosine kinases by inhibiting one or more abnormal tyrosine kinase activities.

BACKGROUND OF THE INVENTION

Cellular signal transduction is a fundamental mechanism whereby external stimuli that regulate diverse cellular processes are relayed to the interior of cells. Reviews describing intracellular signal transduction include Aaronson, *Science*, 254:1146–1153, 1991; Schlessinger, *Trends Biochem. Sci.*, 13:443–447, 1988; and Ullrich and Schiessinger, *Cell*, 61:203–212, 1990. One of the key biochemical mechanisms of signal transduction involves the reversible phosphorylation of tyrosine residues on proteins. The phosphorylation state of a protein is modified through the reciprocal actions of tyrosine kinases (TKs) and tyrosine phosphatases (Tps).

Tyrosine kinases can be of the receptor type (having extracellular, transmembrane and intracellular domains) or the non-receptor type (being wholly intracellular). There are 19 known families of receptor tyrosine kinases including the Her family (EGFR, Her 2, Her 3, Her 4), the insulin receptor family (insulin receptor, IGF-1R, insulin-related receptor), the PDGF receptor family (PDGF-Rα and β, CSF-1R, kit, Flk2), the Flk family (Flk-1, Flt-1, Flk-4), the FGF-receptor family (FGF-Rs 1 through 4), the Met family (Met, Ron), etc. There are 11 known famiolies of non-receptor type tyrosine kinases including the Src family (src, yes, fyn, lyn, lck, blk, Hck, Fgr, yrk), Abl family (Abl, Arg), Zap 70 family (Zap 70, Syk) and Jak family (Jak 1, Jak 2, Tyk 2, Jak 3). Many of these tyrosine kinases have been found to be involved in cellular signalling pathways leading to pathogenic conditions such as cancer, psoriasis, hyperimmune response, etc.

Protein tyrosine kinases play an important role in cellular signaling pathways that regulate the control of cell growth and differentiation (for review, see Schlessinger & Ullrich, 1992, *Neuron*, 9:383–391). Aberrant expression or mutations in receptor tyrosine kinases (RTKs) have been shown to lead to either uncontrolled cell proliferation (e.g. malignant tumor growth) or to defects in key developmental processes. In some instances, a single tyrosine kinase can inhibit, or stimulate, cell proliferation depending on the cellular environment in which it is expressed. Consequently, the biomedical community has expended significant resources to discover the specific biological role of members of the RTK family, their function in differentiation processes, their involvement in tumorigenesis and in other diseases, the biochemical mechanisms underlying their signal transduction pathways activated upon ligand stimulation and the development of novel antineoplastic drugs.

Attempts have been made to identify RTK "inhibitors" using a variety of approaches, including the use of mutant ligands (U.S. Pat. No. 4,966,849), soluble receptors and antibodies (Application No. WO 94/10202; Kendall & Thomas, 1994, *Proc. Nat'l Acad. Sci* 90:10705–09; Kim, et al., 1993, *Nature* 362:841–844), RNA ligands (Jellinek, et al., 19 *Biochemistry* 33:10450–56), protein kinase C inhibitors (Schuchter, et al., 1991, *Cancer Res.* 51:682–687); Takano, et al., 1993, *Mol. Bio. Cell* 4:358A; Kinsella, 20 et al., 1992, *Exp. Cell Res.* 199:56–62; Wright, et al., 1992, *J. Cellular Phys.* 152:448–57) and tyrosine kinase inhibitors (WO 94/03427; WO 92/21660; WO 91/15495; WO 94/14808; U.S. Pat. No. 5,330,992; Mariani, et al., 1994, *Proc. Am. Assoc. Cancer Res.* 25 35:2268).

Attempts have also been made to identify small molecules which act as tyrosine kinase inhibitors. For example, bis monocyclic, bicyclic or heterocyclic aryl compounds (PCT WO 92/20642), vinylene-azaindole derivatives (PCT WO 94/14808) and 1-cycloproppyl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 Al), seleoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer.

SUMMARY OF THE INVENTION

The present invention relates to molecules capable of modulating tyrosine signal transduction to prevent and treat cell proliferative disorders or cell differentiation disorders associated with particular tyrosine kinases by inhibiting one or more abnormal tyrosine kinase activities.

More specifically, the invention is generally directed to compounds having the formulae:

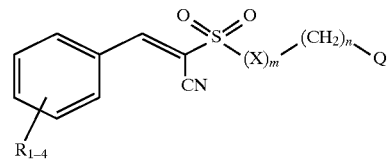

and pharmaceutically acceptable salts thereof, wherein:

X is NH or $CH_2CN$, 20 m is 0 or 1;

n is 0,1, 2, or 3;

Q is an aryl or heteroaryl 5 or 6 member ring optionally substituted with R; $R_{1-4}$ are independently selected from the group consisting of halo, trihalo, methyl, alkyl, alkoxy, hydroxy, H, nitro, cyano, amide, sulfonyl, sulfonamide, carboxy, carboxamide, and amino.

Q is preferably phenyl, thienyl, or

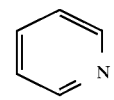

optionally substituted with F or $CF_3$ Examples of preferred compounds include compounds 731–744 shown below:

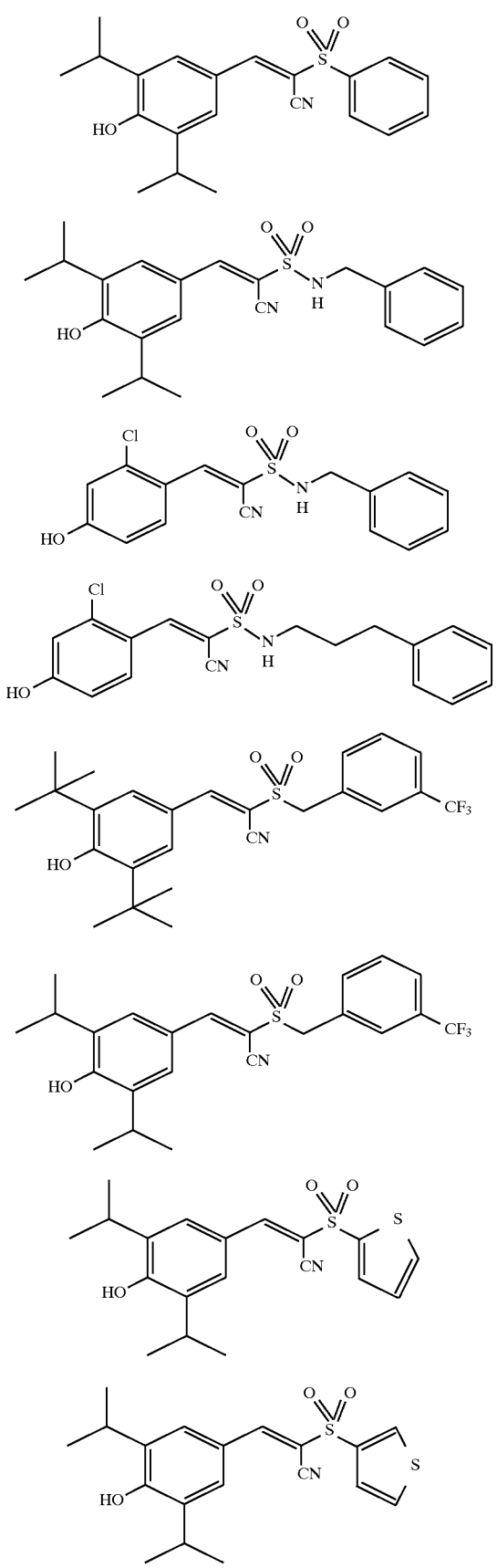

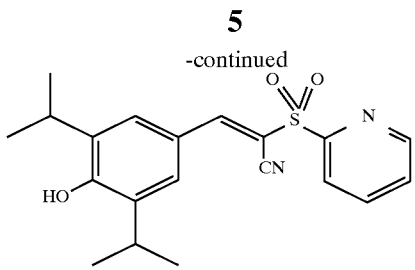

Another preferred compound is 748 shown below:

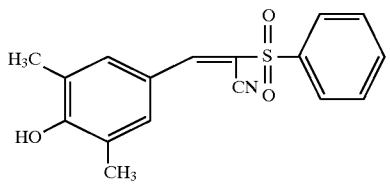

The present invention also provides pharmaceutical compositions and methods for inhibiting cell proliferation or differentiation and related disorders. Examples of such disorders include cancers, blood vessel proliferative disorders, psoriasis, hyperimmune response and fibrotic disorders. Examples of other disorders include the HER2 disorders, EGF disorders, IGFR disorders, PDGFR disorders, met disorders, SVC disorders, and KDR/FLK-1 disorders described herein. It is to be understood that compounds which are effective for diseases related to one RTK will also likely be effective for diseases related to other RTK's, especially those from the same family. Thus, for example, compounds shown to have good effect against Her2 are likely to also have good effect against other members of the Her family, i.e., EGFR, Her3, and Her4.

Chemical Definitions

The following is a list of some of the definitions used in the present disclosure. An "alkyl" group refers to a saturated aliphatic hydrocarbon, including straight-chain, branched-chain, and cyclic alkyl groups. Preferably, the alkyl group has 1 to 12 carbons. More preferably, it is a lower alkyl of from 1 to 7 carbons, more preferably 1 to 4 carbons. The alkyl group may be substituted or unsubstituted. When substituted the substituted group(s) is preferably, hydroxyl, cyano, alkoxy, =O, =S, $NO_2$, $N(CH_3)_2$, amino, or SH.

An "alkenyl" group refers to an unsaturated hydrocarbon group containing at least one carbon-carbon double bond, including straight-chain, branched-chain, and cyclic groups. Preferably, the alkenyl group has 2 to 12 carbons. More preferably it is a lower alkenyl of from 2 to 7 carbons, more preferably 2 to 4 carbons. The alkenyl group may be substituted or unsubstituted. When substituted the substituted group(s) is preferably, hydroxyl, cyano, alkoxy, =O, =S, $NO_2$, halogen, $N(CH_3)_2$, amino, or SH. An "alkynyl" group refers to an unsaturated hydrocarbon group containing at least one carbon-carbon triple bond, including straight-chain, branched-chain, and cyclic groups. Preferably, the alkynyl group has 2 to 12 carbons. More preferably, it is a lower alkynyl of from 2 to 7 carbons, more preferably 2 to 4 carbons. The alkynyl group may be substituted or unsubstituted. When substituted, the substituted group(s) is preferably, hydroxyl, cyano, alkoxy, =O, =S, $NO_2$, $N(CH_3)_2$, amino or SH.

An "alkoxy" group refers to an "—O-alkyl" group, where "alkyl" is defined as described above.

An "aryl" group refers to an aromatic group which has at least one ring having a conjugated pi electron system and includes carbocyclic aryl, heterocyclic aryl and biaryl groups, all of which may be optionally substituted. Preferably, the aryl is a substituted or unsubstituted phenyl or pyridyl. Preferred aryl substituent(s) halogen, trihalomethyl, hydroxyl, SH, OH, $NO_2$, amine, thioether, cyano, alkoxy, alkyl, and amino groups.

An "alkylaryl" group refers to an alkyl (as described above), covalently joined to an aryl group (as described above). Preferably, the alkyl is a lower alkyl.

"Carbocyclic aryl" groups are groups wherein the ring atoms on the aromatic ring are all carbon atoms. The carbon atoms are optionally substituted.

"Heterocyclic aryl" groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted.

An "amide" refers to an —C(O)—NH—R, where R is either alkyl, aryl, alkylaryl or hydrogen.

A "thioamide" refers to —C(S)—NH—R, where R is either alkyl, aryl, alkylaryl or hydrogen. An "ester" refers to an —C(O)—OR', where R' is either alkyl, aryl, or alkylaryl.

An "amine" refers to a —N(R")R'", where R" and R'", is independently either hydrogen, alkyl, aryl, or alkylaryl, provided that R" and R'" are not both hydrogen.

A "thioether" refers to —S—R, where R is either alkyl, aryl, or alkylaryl.

A "sulfonyl" refers to —S(O)$_2$—R, where R is aryl, C(CN)=C-aryl, $CH_2$—CN, alkylaryl, NH-alkyl, NH-alkylaryl, or NH-aryl.

Other features and advantages of the invention will be apparent from the following description of the preferred embodiments thereof and from the claims.

DESCRIPTION OF THE PREFERRED EMBODIMENTS

I. Cell Proliferative and Cell Differentiation Disorders

Cell proliferative and cell differentiiation disorders which can be treated or further studied by the present invention include any disorder associated with a tyrosine kinase signalling pathway, for example cancers, blood vessel proliferative disorders, psoriasis, hyperimmune response and fibrotic disorders. These disorders are not necessarily independent. For example, fibrotic disorders may be related to, or overlap, with blood vessel proliferative disorders. For example, atherosclerosis (which is characterized herein as a blood vessel disorder) results, in part, in the abnormal formation of fibrous tissue.

Blood vessel proliferation disorders refer to angiogenic and vasculogenic disorders generally resulting in abnormal proliferation of blood vessels. The formation and spreading of blood vessels, or vasculogenesis and angiogenesis respectively, play important roles in a variety of physiological processes such as embryonic development, wound healing and organ regeneration. They also play a role in cancer development. Examples of blood vessels disorders include restenosis, retinopathies, and atherosclerosis.

Fibrotic disorders refer to the abnormal formation of extracellular matrix. Examples of fibrotic disorders include hepatic cirrhosis and mesangial cell proliferative disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial cell proliferative disorders refer to disorders brought about by abnormal proliferation of mesangial cells. Mesangial proliferative disorders include various human renal diseases, such as glomerulonephritis, diabetic nephropathy, malignant nephrosclerosis, thrombotic microangiopathy syndromes, transplant rejection, and glomerulopathies. PDGFR has been implicated in the maintenance of mesangial cell proliferation. (Floege, J. et al., *Kidney International* 43S:47–54 (1993))

HER2, EGFR, IGFR, PDGFR, met, src and KDR/FLK-1 driven cancers and disorders are described in detail below and are a preferred subset of the disorders to be treated. A cancer cell refers to various types of malignant neoplasms, most of which can invade surrounding tissues, and may metastasize to different sites, as defined by Stedman's Medical Dictionary 25th edition (Hensyl ed. 1990).

A. HER2 Cell Proliferation Disorders

The HER-2 protein is a member of the class I receptor tyrosine kinase (RTK) family. Yarden and Ullrich, *Annu. Rev. Biochem.* 57:443, 1988; Ullrich and Schiessinger, *Cell* 61:203, 1990. HER-2 protein is structurally related to EGF-R, p180(HER-3), and p180(HER-4). Carraway, et al., *Cell* 78:5, 1994; Carraway, et al., *J. Biol. Chem.* 269:14303, 1994. These receptors share a common molecular architecture and contain two cysteine-rich regions within their cytoplasmic domains and structurally related enzymatic regions within their cytoplasmic domains.

Activation of HER-2 protein can be caused by different events such as ligand-stimulated homodimerization, ligand-stimulated hetero-dimerization and ligand-independent homo-dimerization. Ligand-stimulated hetero-dimerization appears to be induced by EGF-R to form EGF-R/HER2 complexes and by neu differentiation factor/heregulin (NDF/HRG) to form HER-2/HER-3 and/or HER2/HER-4 complexes. Wada et al., *Cell* 61:1339, 1990; Slikowski et al., *J. Biol. Chem.* 269:14661, 1994; Plowman et al., *Nature* 266:473, 1993. Ligand-dependent activation of HER-2 protein is thought to be mediated by neuactivating factor (NAF) which can directly bind to p165(HER-2) and stimulate enzymatic activity. Dougall et al., *Oncogene* 9:2109, 1994; Samata et al., *Proc. Natl. Acad. Sci. USA* 91:1711, 1994. Ligand-independent homodimerization of HER-2 protein and resulting receptor activation is facilitated by over-expression of HER-2 protein.

HER-2 protein substrates are acted upon by activated HER-2 complexes such as HER-2/EGF-R, HER-2/HER-2, HER2/HER-3, and HER-2/HER-4 activated complexes. An activated HER-2 complex acts as a phosphokinase and phosphorylates different cytoplasmic proteins. Examples of HER-2 substrates include $IP_3$ kinase and PI 4-kinase. Scott et al., *Journal of Biological Chemistry* 22:14300, 1991. Proteins bind to an activated HER-2 complex and then another protein. For example, GRB-7 binding to a HER-2 complex may be sufficient to initiate the GRB-7 signaling pathway without phosphorylation. Stein et al., *EMBO Journal* 13:1331, 1993.

Thus, HER-2 protein activities include: (1) phosphorylation of HER-2 protein, HER-3 protein or HER-4 protein; (2) phosphorylation of a HER-2 protein substrate; (3) interaction with a HER-2 adapter protein; and/or (4) HER-2 protein surface expression. Additional HER-2 protein activities can be identified using standard techniques. For example, a partial agonistic monoclonal antibody recognizing HER-2 protein can be used to activate HER-2 protein and examine signal transduction of HER-2 protein. Scott et al., *Journal of Biological Chemistry* 22:14300,1991. HER2 activity can be assayed by measuring one or more of the following activities: (1) phosphorylation of HER2; (2) phosphorylation of a HER2 substrate; (3) activation of an HER2 adapter molecule; and (4) increased cell division. These activities can be measured using techniques described below and known in the art.

HER2 driven disorders are characterized by inappropriate or over-activity of HER2. Inappropriate HER-2 activity refers to either: (1) HER2 expression in cells which normally do not express HER2; (2) increased HER-2 expression leading to unwanted cell proliferation such as cancer; (3) increased HER-2 activity leading to unwanted cell proliferation, such as cancer; and/or overactivity of HER-2. Over-activity of HER2 refers to either an amplification of the gene encoding HER2 or the production of a level of HER2 activity which can be correlated with a cell proliferative disorder (i.e., as the level of HER2 increases the severity of one or more of the symptoms of the cell proliferative disorder increases). HER2 driven disorders are typically cell proliferative or differentiation disorders such as cancers. HER2 driven disorders appear to be responsible for a sub-population of different types of cancers. For example, as noted above, Slamon et al., found about 30% of breast cancer cells to have increased HER2 gene expression. Slamon et al., also found a correlation between her2 (c-erbB-2) amplification and poor patient prognosis.

Treatment of patients suffering from a HER2 disorder is facilitated by first determining whether the cell proliferative disorder is characterized by an overactivity of HER2. After the disorder is identified, patients suffering from such a disorder can be identified by analysis of their symptoms using procedures well known to medical doctors. Such identified patients can then be treated as described herein. The use of the present invention to treat breast cancer is preferred because of the prevalence and severity of breast cancer. Carcinoma of the breast is the most common cancer among women and their second leading cause of cancer death (Marshall, E., *Science* 259:618–621, 1993). The incidence of breast cancer has been increasing over the past several decades (Marshall, supra, and Harris, J. R., et al, *New Engl. J . Med.*, 327(5):319–328, 1992). In addition to breast cancers, increased HER2 activity or gene expression has been associated with certain types of blood cancers, stomach adenocarcinomas, salivary gland adenocarcinomas, endometrial cancers, ovarian adenocarcinomas, gastric cancers, colorectal cancers, non-small cell lung cancer, and glioblastomas. The methods described herein can be used to identify the sub-populations of these different cancers which are characterized by over-activity of HER2.

B. EGFR Disorders

Some of the featured compounds can be used to treat cell proliferative and/or cell differentiation disorders characterized by inappropriate EGFR activity. "Inappropriate EGFR" activity refers to either: (1) EGF-receptor (EGFR) expression in cells which normally do not express EGFR; (2) EGF expression by cells which normally do not express EGF; (3) increased EGF-receptor (EGFR) expression leading to unwanted cell proliferation; (4) increased EGF expression leading to unwanted cell proliferation; and/or (5) mutations leading to constitutive activation of EGF-receptor (EGFR) The existence of inappropriate or abnormal EGF and EGFR levels or activities is determined by procedures well known in the art.

An increase in EGF activity or expression is characterized by an increase in one or more of the activities which can occur upon EGF ligand binding such as: (1) EGF-R dimerization; (2) auto-phosphorylation of EGFR, (3) phosphorylation of an EGFR substrate (e.g., PLC, see Fry supra), (4)

activation of an adapter molecule, and/or (5) increased cell division. These activities can be measured using techniques described below and known in the art. For example autophosphorylation of EGFR can be measured as described in the examples below using an anti-phosphotyrosine antibody, and increased cell division can be performed by measuring $^3$H-thymidine incorporation into DNA. Preferably, the increase in EGFR activity is characterized by an increased amount of phosphorylated EGFR and/or DNA synthesis.

Unwanted cell proliferation and/or differentiation can result from inappropriate EGFR activity occurring in different types of cells including cancer cells, cells surrounding a cancer cell, and endothelial cells. Examples of disorders characterized by inappropriate EGF activity include cancers such as glioma, head, neck, gastric, lung, breast, ovarian, colon, and prostate; and other types of cell proliferative disorders such as psoriasis.

C. IGF Disorders

The insulin-like growth factor I receptor belongs to the family of transmembrane tyrosine kinase receptors such as platelet-derived growth factor receptor, the epidermal growth factor receptor, and the insulin receptor. The insulin-like growth factor family of ligands, receptors and binding proteins is reviewed in Krywicki and Yee, *Breast Cancer Research and Treatment*, 22:7–19, 1992.

IGF-1 R has been implicated as an absolute requirement for the establishment and maintenance of the transformed phenotype both in vitro and in vivo in several cell types. Baserga R., *Cancer Research* 55:249–252, 1995. Herbimycin A has been said to inhibit the IGF-1R protein tyrosine kinase and cellular proliferation in human breast cancer cells. Sepp-Lorenzino et al., Abstract, 1994. Experiments studying the role of IGF-1R in transformation have used antisense strategies, dominant negative mutants, and antibodies to the IGF-1R and have led to the suggestion that IGR-1R may be a preferred target for therapeutic interventions.

IGF driven disorders are characterized by inappropriate or over-activity of IGF. Inappropriate IGF activity refers to either: (1) IGF expression in cells which normally do not express IGF; (2) increased IGF expression leading to unwanted cell proliferation such as cancer; (3) increased IGF activity leading to unwanted cell proliferation, such as cancer; and/or over-activity of IGF. Over-activity of IGF refers to either an amplification of the gene encoding IGF or the production of a level of IGF activity which can be correlated with a cell proliferative disorder (i.e., as the level of IGF increases the severity of one or more of the symptoms of the cell proliferative disorder increases). Examples of IGF driven disorders include the various IGF related human malignancies reviewed in Cullen et al., *Cancer Investigation*, 9(4):443–454, 1991, incorporated herein by reference in its entirety, including any drawings. IGF's clinical importance and role in regulating osteoblast function is reviewed in Schmid, *Journal of Internal Medicine*, 234:535–542, 1993.

Thus, IGF activities include: (1) phosphorylation of IGF protein; (2) phosphorylation of a IGF protein substrate; (3) interaction with a IGF adapter protein; and/or (4) IGF protein surface expression. Additional IGF protein activities can be identified using standard techniques. IGF activity can be assayed by measuring one or more of the following activities: (1) phosphorylation of IGF; (2) phosphorylation of a IGF substrate; (3) activation of an IGF adapter molecule; and (4) increased cell division. These activities can be measured using techniques described below and known in the art.

D. KDR/FLK-1 Disorders

Two structurally related RTKs have been identified to bind VEGF with high affinity: the fms-like tyrosine 1 (fit-l) receptor (Shibuya et al., 1990, oncogene 5:519–524; De Vries et al., 1992, Science 255:989–991) and the KDR/FLK-1 receptor. Vascular endothelial growth factor (VEGF) has been reported to be an endothelial cell specific mitogen with in vitro endothelial cell growth promoting activity. Ferrara & Henzel, 1989, Biochein. Biophys. Res. Comm. 161:851–858; Vaisman et al., 1990, J. Biol. Chem. 265:19461–19566. Information set forth in U.S. application Ser. Nos. 08/193,829, 08/038,596 and 07/975,750, strongly suggest that VEGF is not only responsible for endothelial cell proliferation, but also is the prime regulator of normal and pathological angiogenesis. See generally, Klagsburn & Soker, 1993, Current Biology 3(10)699–702; Houck, et al., 1992, J. Biol. Chem. 267:26031–26037.

Normal vasculogenesis and angiogenesis play important roles in a variety of physiological processes such as embryonic development, wound healing, organ regeneration and female reproductive processes such as follicle development in the corpus luteum during ovulation and placental growth after pregnancy. Folkman & Shing, 1992, J. Biological Chem. 267(16) :10931–34. Uncontrolled vasculogenesis and/or angiogenesis has been associated with diseases, such as diabetes, as well as malignant solid tumors that rely on vascularization for growth. Klagsburn & Soker, 1993, Current Biology 3(10) :699–702; Folkham, 1991, J. Natl., Cancer Inst. 82:4–6; Weidner, et al., 1991, New Engl. J. Med. 324:1–5.

The surmised role of VEGF in endothelial cell proliferation and migration during angiogenesis and vasculogenesis indicate an important role for the KDR/FLK-1 in these processes The invention is further based on the observation that diseases such as diabetes mellitus (Folkman, 198, in XIth Congress of Thrombosis and Haemostasis (Verstraeta, et al., eds.) pp. 583–596, Leuven University Press, Leuven) and arthritis, as well as malignant tumor growth may result from uncontrolled angiogenesis. See e.g., Folkman, 1971, *N. Engl. J. Med*. 285:1182–1186. The receptors to which VEGF specifically binds are an important and powerful therapeutical target for the regulation and modulation of vasculogenesis and/or angiogenesis and a variety of severe diseases which involve abnormal cellular growth caused by such processes. Plowman, et al., 1994, *DN&P* 7(6) :334–339. More particularly, the KDR/FLK-1 receptor's high specificity and role in the neovascularization make it a very distinct and powerful target for therapeutic approaches for the treat cancer and other diseases which involve the uncontrolled formation of blood vessels.

The present invention relates to compounds capable of regulating and/or modulating tyrosine signal transduction and more particularly KDR/FLK-1 receptor signal transduction in order to inhibit or promote angiogenesis and/or vasculogenesis. The invention is based upon the discovery and design of compounds that inhibit, prevent, or interfere with the signal transduced by KDR/FLK-1 when activated by ligands such as VEGF. Although it is therefore believed that the compounds of the present invention act on a receptor or other component along the tyrosine kinase signal transduction pathway, the compounds may also act directly on the tumor cells that result from uncontrolled angiogenesis.

For purposes of this application, although the nomenclature of the human and murine counterparts of the generic "flk-I" receptor differ, they are, in many respects, interchangeable. The murine receptor, FLK1, and its human counterpart, KDR, share a sequence homology of 93.4% within the intracellular domain. Likewise, murine FLK-I binds human VEGF with the same affinity as mouse VEGF, and accordingly, is activated by the ligand derived from either species. Millauer et al., 1993, *Cell* 72:835–846; Quinn et al., 1993, *Proc. Natl. Acad. Sci. USA* 90:7533–7537. FLK-1 also associates with and subsequently tyrosine phosphorylates human RTK substrates (e.g., PLC-γ or p85) when coexpressed in 293 cells (human embryonal kidney fibroblasts).

Models which rely upon the FLK-1 receptor therefore are directly applicable to understanding the KDR receptor. For example, use of the murine FLK-1 receptor in methods to identify compounds which regulate the signal transduction pathway are directly applicable to the identification of compounds which may be used to regulate the human signal transduction pathway, and more specifically, activity related to the KDR receptor. Chemical compounds identified as inhibitors of KDR/FLK-1 in vitro, will be confirmed in suitable in vivo models. Both in vivo mouse and rat animal models have been demonstrated to be of excellent value for the examination of the clinical potential of agents acting on the KDR/FLK-1 induced signal transduction pathway.

This invention is therefore directed to compounds which regulate, modulate and/or inhibit vasculogenesis and/or angiogenesis by affecting the enzymatic activity of the KDR/FLK-1 receptor and interfering with the signal transduced by KDR/FLK-1. More particularly, the present invention is directed to compounds which regulate, modulate and/or inhibit the KDR/FLK-1 mediated signal transduction pathway as a therapeutic approach to cure many kinds of solid tumors, including but not limited to glioblastoma, melanoma and Kaposi's sarcoma, and ovarian, lung, mammary, prostate, pancreatic, colon and epidermoid carcinoma. In addition, data suggest the administration of compounds which inhibit the KDR/FLK1 mediated signal transduction pathway may be used for the treatment of hemangioma and diabetic retinopathy.

The invention also relates to the inhibition of vasculogenesis and angiogenesis via other receptor-mediated pathways, including the pathway comprising the highly related flt-1 receptor. Receptor tyrosine kinase mediated signal transduction is initiated by extracellular interaction with a specific growth factor (ligand), followed by receptor dimerization, transient stimulation of the intrinsic protein tyrosine kinase activity and autophosphorylation. Binding sites are thereby created for intracellular signal transduction molecules and lead to the formation of complexes with a spectrum of cytoplasmic signalling molecules that facilitate the appropriate cellular response. (E.g., cell division, metabolic effects to the extracellular microenvironment) See, Schlessinger and Ullrich, 1992, *Neuron* 9:1–20.

The close homology of the intracellular regions of KDR/FLK-1 with that of the PDGF-β-Receptor (50.3% homology) and/or the highly related flt-1 receptor indicates the induction of overlapping signal transduction pathways. For example, for the PDGF-βReceptor, members of the src family (Twamley et al., 1993, *Proc. Natl. Acad. Sci. USA* 90:7696–7700), phosphatidylinositol-3'-kinase (Hu et al., 1992, *Mol. Cell. Biol.* 12:981–990), phospholipase c-γ (Kashishian & Cooper, 1993, *Mol. Cell. Biol.* 4:49–51), ras-GTPase-activating protein, (Kashishian et al., 1992, *EMBO J.* 11:1373–1382), PTP-ID/syp (Kazlauskas et al., 1993, *Proc. Natl. Acad. Sci. USA* 10 90:6939–6943), Grb2 (Arvidsson et al., 1994, *Mol. Cell. Biol.* 14:6715–6726), and the adapter molecules Shc and Nck (Nishimura et al., 1993, *Mol. Cell. Biol.* 13:6889–6896), have been shown to bind to regions involving different autophosphorylation sites. See generally, Claesson-Welsh, 1994, prog. Growth Factor Res. 5:37–54. Thus, it is likely that signal transduction pathways activated by KDR/FLK-1 include the ras pathway (Rozakis et al., 1992, *Nature* 360:689–692), the PI-3'-kinase pathway and the src-mediated and plcγ-mediated pathways. Each of these pathways may play a critical role in the angiogenic and/or vasculogenic effect of KDR/FLK-1 in endothelial cells. Consequently, the present invention is also directed to the use of the organic compounds discussed herein to modulate angiogenesis and vasculogenesis as such processes are controlled by these pathways.

E. C-MET Related Disorders

The c-met protooncogene is a growth factor receptor with tyrosine kinase activity and a suspected involvement in hepatocarcinogenesis. C-met protein expression has been correlated with poor to moderate differentiation of cancer cells whereas in one study all cases have increased to more proliferative activity showed c-met protein expression. Thus, suggesting an important role in the development of hepatocellular carcinoma see Suzuki et al., *Hepatology* 20:1231–1236, 1994.

The met gene is selectively expressed in several epithelial tissues and high levels of met mRNA have been found in liver, gastrointestinal tract, thyroid and kidney. Normal or increased levels of met mRNA and met Protein were consistently found in fresh samples of carcinomas as well as epithelial tumor cell lines and in thyroid carcinomas of a specific histiotype. The amount of met protein was found to be increased more than 100 fold suggesting a role in growth control of epithelial cells other than hepatocytes and suggesting the increase in expression may convert growth advantage to neoplasm cells. Renzo et al., *Oncogene* 6:1997–2003, 1991.

The c-met oncogene is expressed not only in hepatocytes but also in a variety of tissues and over expression of c-met is found in some cell lines and tumors. It is amplified and overexpressed in a gastric carcinoma cell line, gtl-16 and it has been reported that the expression of c-met is enhanced in colorectal, gastric and thyroid cancer. The met gene is overexpressed in some cases of human leukemia and lymphoma. See Jucker et al. *Leukemia Res.*, 18:7–16, 1994. Expression of the met gene was detected in patients with Hodgkins disease, Burkitt's, lymphoma cell line and acute myeloid leukemia. Expression of c-met encoded HGFR in human melonocytic neoplasms has been used to demonstrate the relationship to malignant tumor progressions. Natali, *Br. J. Cancer* 68:746–750, 1993.

The role of c-met in human tumors is review in Giordano et al., *European Jrnl. Cancer Prevention*, 1:45–49, 1992. Examples of human tumors believed to be associated with c-met include colon cancer tumor, epithelial tumors, gastrointestinal tumors, thyroid tumors, and others. The expression of HGFR in human pancreatic cancer is described in Renzo et al., *Cancer Res.*, 55:1129–1138, 1995. The TPR/MET oncogenic rearrangement is present and expressed in human gastric carcinoma and precursor legion, see Soman et al., *Proc. Nati. Acad. Sci. USA*, 88:4892–4896, 1991. It has been reported that HGF gene deletion leads to death knockout mice see *Bioworld Today* Feb. 24, 1995. The molecular characteristics of HGF-SF and its role in cell motility and invasion is reviewed in Widner et al., *Hepatocyte Growth Factor Scatter Factor (HGSF) and the C MET Receptor* Editors Goldberg and Rosen, 1993.

F. PDGFR Driven Disorders

PDGFR driven disorders are described in U.S. patent application Ser. Nos. 08/370,574 and 08/426,789, filed Jan. 6, 1995 and Apr. 21, 1995, both of which are incorporated herein by reference in their entirety including any drawings.

II. Diagnostic uses

Another use of the compounds described herein is to help diagnose whether a disorder is driven, to some extent, by a particular receptor tyrosine kinase. Some cancers may be driven by more than one receptor tyrosine kinases. For example, Wada et al., *Oncogene* 5:489–495, 1990, describes co-expression of EGFR and HER2.

A diagnostic assay to determine whether a particular cancer is driven by a specific receptor can be carried out using the following steps: (1) culturing test cells or tissues; (2) administering a compound which can inhibit one or more receptor tyrosine kinase; and (3) measuring the degree of growth inhibition of the test cells.

These steps can be carried out using standard techniques in light of the present disclosure. For example, standard techniques can be used to isolate cells or tissues and culturing or in vivo. An example of an in vitro assay is a cellular kinase assay as described below. An example of an in vivo assay is a xenograft experiment where the cells or tissues are implanted into another host such as a mouse.

Compounds of varying degree of selectivity are useful for diagnosing the role of a receptor tyrosine kinase. For example, compounds which inhibit more than one type of receptor tyrosine kinase can be used as an initial test compound to determine if one of several receptor tyrosine kinases drive the disorder. More selective compounds can then be used to further eliminate the possible role of different receptor tyrosine kinases in driving the disorder. Test compounds should be more potent in inhibiting receptor tyrosine kinase activity than in exerting a cytotoxic effect (e.g., an $IC_{50}LD_{50}$ of greater than one). $IC_{50}$ and $LD_{50}$. can be measured by standard techniques, such as described in the present application and using an MTT assay as described by Mossman supra, or by measuring the amount of LDH released (Korzeniewski and Callewaert, J. supra; Decker and Lohmann-Matthes, supra). The degree of $IC_{50}LD_{50}$ of a compound should be taken into account in evaluating the diagnostic assay. Generally, the larger the ratio the more reliable the information. Appropriate controls to take into account the possible cytotoxic effect of a compound, such as treating cells not associated with a cell proliferative disorder (e.g., control cells) with a test compound, can also be used as part of the diagnostic assay.

III. Pharmaceutical Formulations and Modes of Administration

The particular compound that affects the protein complexes and the disorder of interest can be administered to a patient either by themselves, or in pharmaceutical compositions where it is mixed with suitable carriers or excipient(s). In treating a patient exhibiting a disorder of interest, a therapeutically effective amount of a agent or agents such as these is administered. A therapeutically effective dose refers to that amount of the compound that results in amelioration of symptoms or a prolongation of survival in a patient.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture (i.e., the concentration of the test compound which achieves a half-maximal disruption of the protein complex, or a half-maximal inhibition of the cellular level and/or activity of a complex component). Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in *The Pharmacological Basis of Therapeutics*, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in *Remington's Pharmaceutical Sciences*, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few. For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push- fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; eg the concentration necessary to achieve a 50–90% inhibition of the kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90%.

EXAMPLES

Examples are provided below to illustrate different aspects and embodiments of the present invention. These examples are not intended in any way to limit the disclosed invention. Rather, they illustrate methodology by which drugs having the disclosed formulas can be readily identified by routine procedure to ensure that they have the desired activity, and the synthesis of different compounds described herein. Compounds within a formula claimed herein can be screened to determine those with the most appropriate activity prior to administration to an animal or human. Other compounds can also be screened to determine suitability for use in methods of this invention.

4-Fluorophenylsulphonylacetonitrile, 2,4-difluorophenylsulphonylacetonitrile, 4-trifluoromethylphenylsulphonylacetonitrile and 3-trifluoromethylsulphonylacetonitrile were prepared by oxidation of 4-fluorophenylmercaptoacetonitrile, 2,4-difluorophenylmercaptoacetonitrile, 4-trifluoromethylphenylmercaptoacetonitrile and 3-trifluoromethylphenylmercaptoacetonitrile with OXONE (trade mark), respectively. 4-Trifluoromethylphenylmercaptoacetonitrile and 3-trifluoromethylphenylmercaptoacetonitrile were prepared by reacting the corresponding thiophenol with bromoacetonitrile in acetone with potassium carbonate as the base.

All other sulphonylacetonitriles are commercially available.

Example 1

(E)-3-(3,5-Diisopropyl-4-hydroxyphenyl)-2-[(pyrid-2-yl)sulfonyl]acrylonitrile

The reaction mixture of 450.0 mg of 3,5-diisopropyl-4-hydroxylbenzaldehyde, 400.0 mg of 2-pyridinesulphonylacetonitrile and a few drops of piperidine in 10.0 mL of ethanol was refluxed for 3 h and then cooled to room temperature. To the above reaction mixture was added 5.0 mL of water until crystallization began. After standing at 0° C. for 2 h, the solid was filtered, washed with

Example 2

(E)-2—Cyanomethylsulfonyl-3-(3,5-diisopropyl-4-hydroxyphenyl)acrylonitrile

A mixture of 500 mg of 3,5-diisopropyl-4-hydroxybenzaldehyde and 700 mg of sulphonyl diacetonitrile in 6 ml of ethanol was refluxed with a few drops of piperidine for 4 hours. Ethanol was removed in a rotavap and the mixture worked up with ethyl acetate, diluted acid and brine. A portion of the crude was then purified by HPLC on a C-18 column to provide 50 mg of the titled compound along with 30 mg of (E,E)-2-[[1—Cyano-2-(3,5-diisopropyl-4-hydroxyphenyl)ethenyl]sulfonyl]-3-(3,5-diisopropyl-4-hydroxyphenyl)acrylonitrile.

Example 3

(E,E)-2-[[1—Cyano-2-(3,5-diisopropyl-4-hydroxyphenyl)ethenyl]sulfonyl]-3-(3,5-diisopropyl-4-hydroxyphenyl)acrylonitrile The titled compound was obtained in the preparation of EXAMPLE 2.

Example 4

(E)-3-(3,5-Diisopropyl-4-hydroxyphenyl)-2-(phenylsulfonyl)acrylonitrile

The titled compound was prepared with 3,5-diisopropyl-4-hydroxybenzaldehyde and phenylsulphonly acetonitrile under the similar conditions as described for EXAMPLE 1.

Example 5

(E)-3-(3,5-Dimethyl-4-hydroxyphenyl)-2-(phenylsulfonyl)acrylonitrile

The titled compound was prepared with 3,5-dimethyl-4-hydroxybenzaldehyde and phenylsulphonly acetonitrile under the similar conditions as decribed for EXAMPLE 1.

Example 6

(E)-3-(3,5-Dimethyl-4-hydroxyphenyl)-2-[(pyrid-2-yl)sulfonyl]acrylonitrile

The titled compound was prepared with 3,5-dimethyl-4-hydroxybenzaldehyde and (pyrid-2-yl)sulphonyl acetonitrile under the similar conditions as described for EXAMPLE 1.

Example 7

(E)-3-(3,5-Di-t-butyl-4-hydroxyphenyl)-2-(phenylsulfonyl)acrylonitrile

The titled compound was prepared with 3,5-di-t-butyl-4-hydroxybenzaldehyde and phenylsulphonly acetonitrile under the similar conditions as described for EXAMPLE 1.

Example 8

(E)-3-(3,5-Di-t-butyl-4-hydroxyphenyl)-2-[(pyrid-2-yl)sulfonyl]acrylonitrile

The titled compound was prepared with 3,5-di-t-butyl-4-hydroxybenzaldehyde and (pyrid-2-yl)sulphonyl acetonitrile under the similar conditions as described for EXAMPLE 1.

Example 9

(E)-3-(3,5-Di-t-butyl-4-hydroxyphenyl)-2-(cyanomethylsulfonyl)acrylonitrile

The titled compound was prepared with 3,5-di-t-butyl-4-hydroxybenzaldehyde and sulphonyl diacetonitrile under the similar condition as described for EXAMPLE 2.

Example 10

(E,E)-2-[[1—Cyano-2-(3,5-diisopropyl-4-hydroxyphenyl)ethenyl]sulfonyl]-3-(3,5-di-t-butyl-4-hydroxyphenyl)acrylonitrile The titled compound was obtained in the preparation of EXAMPLE 9.

Example 11

(E,E)-[1-Cyano-2-(3,5-dimethyl-4-hydroxyphenyl)ethenyl]sulfonyl-(3,5-dimethyl-4-hydroxyphenyl)acrylonitrile The titled compound was prepared with 3,5-dimethyl-4-hydroxybenzaldehyde and sulphonyl diacetonitrile under the similar conditions as described for EXAMPLE 3.

Example 12

(E)-2-(Benzylaminosulfonyl)-3-(3,5-di-t-butyl-4-hydroxyphenyl)acrylonitrile

A: To a solution of 2.14 g of benzylamine in 10 ml of ether at 5° C. was slowly added a solution of 1.37 g of cyanomethylsulfonylchloride [Sammes, Wylie, Hoggett, *J. Chem. Soc.* (C), 2151, 1971] in 5 ml of ether. The resulting mixture was then stirred for another 30 minutes, poured into 50 ml of water and extracted with 50 ml of ethyl acetate. The organic layer was then washed with brine, dried over magnesium sulfate, filtered and concentrated. The crude sulfonamide was then purified on a silica gel column (1:1 hexane/ethyl acetate) to provide 1.52 g of N-benzyl cyanomethylsulfonamide.

B: A mixture of 250 mg of 3,5-di-t-butyl-4-hydroxybenzaldehyde and 230 mg of N-benzyl cyanomethyl sulfonamide in 2 ml of ethanol with 2 drops of piperidine was heated at 100° C. for 3 hours. The cooled mixture was then diluted with 10 ml of water and extracted with 50 ml of ethyl acetate. The organic extract was then washed with brine, dried over sodium sulfate, filtered and concentrated. Crystallization of the crude with ethyl acetate and hexane yield 206 mg of the titled compound.

Example 13

(E)-2-(Benzylaminosulfonyl)-3-(3,5-diisopropyl-4-hydroxyphenyl)acrylonitrile

The titled compound was prepared with 3,5-diisopropyl-4-hydroxybenzaldehyde and N-benzyl cyanomethylsulfonamide under the similar conditions as described for EXAMPLE 12 (part B).

Example 14

(E)-2-(Benzylaminosulfonyl)-3-(3,5-dimethyl-4-hydroxyphenyl)acrylonitrile

The titled compound was prepared with 3,5-dimethyl-4-hydroxybenzaldehyde and N-benzyl cyanomethylsulfonamide under the similar conditions as described for EXAMPLE 12 (part B).

Example 15

(E)-3-(3,5-Di-t-butyl-4-hydroxyphenyl)-2-[(3-phenyl-n-propyl)aminosulfonyl]acrylonitrile A: N-3-Phenyl-n-propyl cyanomethylsulfonamide was prepared with 3-phenyl-n-propylamine and cyanomethylsulphonyl chloride under the similar conditions as decribed for N-benzyl cyanomethylsulfonamide (Part A, EXAMPLE 12).

B: N-3-Phenyl-n-propyl cyanomethylsulfonamide and 3,5-di-t-butyl-4-hydroxybenzaldehyde was condensed under the similar conditions as described for example 12 (Part B) to yield the titled compound.

Example 16

(E)-3-(3,5-Diisopropyl-4-hydroxyphenyl)-2-[(3-phenyl-n-propyl)aminosulfonyl]acrylonitrile):

The titled compound was prepared with 3,5-diisopropyl-4-hydroxybenzaldehyde and N-3-phenyl-n-propyl cyanomethylsulfonamide under the similar conditions as described for EXAMPLE 12 (part B).

Example 17

(E)-3-(3,5-Dimethyl-4-hydroxyphenyl)-2-[(3-phenyl-n-propyl)aminosulfonyl]acrylonitrile The titled compound was prepared with 3,5-dimethyl-4-hydroxybenzaldehyde and N-3-phenyl-n-propyl cyanomethylsulfonamide under the similar conditions as described for EXAMPLE 12 (part B).

Example 18

(E)-3-(3-t-Butyl-4-hydroxyphenyl)-2-(4-fluorophenylsulfonyl)acrylonitrile

The reaction mixture of 178.0 mg of 3-t-butyl-4-hydroxybenzaldehyde and 219.0 mg of (4-fluorobenzenesulphonyl)acetonitrile in 2.0 mL of ethanol containing 0.01 mL piperidine was refluxed for 4 h and cooled down. To the above reaction mixture was added water and then the aqueous layer was extracted with ethyl acetate. The organic layer was washed with brine, dried over magnesium sulfate and concentrated. The resulting residue was purified on silica gel column eluting with ethyl acetate-hexane (1:6) to give 295.0 mg of the titled compound.

Example 19

(E)-3-(3-Bromo-5-t-butyl-4-hydroxyphenyl)-2-[(pyrid-2-yl)sulfonyl]acrylonitrile

The reaction mixture of 258.0 mg of 3-bromo-5-t-butyl-4-hydroxybenzylaldehyde, 219.0 mg of (pyrid-2-yl) sulphonylacetonitrile and 2 drops of piperidine in 2.0 mL of ethanol was refluxed for 2 h and cooled down in ice-water. The yellow precipitate was filtered, washed with cold ethanol, and dried in oven at 40° C. overnight to afford 365.0 mg of the titled compound.

The following compounds were prepared by the same methods as described above.

Example 20

(E)-3-(3-Bromo-4,5-dihydroxyphenyl)-2-(phenylsulfonyl)acrylonitrile

Example 21

(E,E)-3-(3,5-Diisopropyl-4-hydroxyphenyl)-2-[[2-(3,5-disopropyl-4-hydroxyphenyl)-1-cyanoethenyl]sulfonyl]acrylonitrile

Example 22

(E,E)-2-[2-(3-Bromo-4,5-dihydroxyphenyl)-1-cyanoethenylsulfonyl]-3-(3-bromo-4,5-dihydroxyphenyl)acrylonitrile

Example 23

(E)-2-Cyanomethylsulfonyl-3-(3-bromo-4,5-dihydroxyphenyl)acrylonitrile

Example 24

(E)-3-(3,4-Dihydroxyphenyl)-2-[(pyrid-2-yl)sulfonyl]acrylonitrile

Example 25

(E)-2-Cyanomethylsulfonyl-3-(4-hydroxy-3,5-dimethylphenyl)acrylonitrile

Example 26

(E,E)-[1-Cyano-2-(3,5-dimethyl-4-hydroxyphenyl)ethenyl]sulfonyl-(3,5-dimethyl-4-hydroxyphenyl)acrylonitrile

Example 27

(E)-3-(3,4-Dihydroxyphenyl)-2-(phenylsulfonyl)acrylonitrile

Example 28

(E)-2-(Benzylaminosulfonyl)-3-(3,4-dihydroxyphenyl)acrylonitrile

Example 29

(E)-2-(Benzylaminosulfonyl)-3-(4-hydroxy-3-ethoxyphenyl)acrylonitrile

Example 30

(E)-2-(Benzylaminosulfonyl)-3-(3-bromo-4,5-dihydroxyphenyl)acrylonitrile

Example 31

(E)-3-(3-Bromo-4,5-dihydroxyphenyl)-2-[(4-phenyl-n-butyl)aminosulfonyl]acrylonitrile

Example 32

(E)-3-(3-Ethoxy-4-hydroxyphenyl)-2-[(3-phenyl-n-propyl)aminosulfonyl]acrylonitrile

Example 33

(E)-3-(3,4-Dihydroxyphenyl)-2-[(3-phenyl-n-propyl)aminosulfonyl]acrylonitrile

Example 34

(E)-3-(4-Hydroxy-3-ethoxyphenyl)-2-(phenylsulfonyl)acrylonitrile

Example 35

(E)-3-(3-Ethoxy-4-hydroxyphenyl)-2-[(pyrid-2-yl)sulfonyl]acrylonitrile

Example 36

(E)-3-(3,5-Di-t-butyl-4-hydroxyphenyl)-2-[3-(trifluoromethyl)benzylsulfonyl]acrylonitrile

Example 37

(E)-3-(3,5-Diisopropyl-4-hydroxyphenyl)-2-[3-(trifluoromethyl)benzylsulfonyl]acrylonitrile

Example 38

(E)-3-(3-Ethoxy-4-hydroxyphenyl)-2-[(3-trifluoromethyl)benzylsulfonyl]acrylonitrile

Example 39

(E)-3-(3-Bromo-4,5-dihydroxyphenyl)-2-[3-(trifluoromethyl)benzylsulfonyl]acrylonitrile

Example 40

(E)-3-(3,5-Dimethyl-4-hydroxyphenyl)-2-[3-(trifluoromethyl)benzylsulfonyl]acrylonitrile

Example 41

(E)-3-(3,4-Dihydroxyphenyl)-2-[3-(trifluoromethyl)benzylsulfonyl]acrylonitrile

Example 42

(E)-2-(4-Fluorophenylsulfonyl)-3-(4-hydroxy-3,5-di-t-butylphenyl)acrylonitrile

Example 43

(E)-3-(3,5-Diisopropyl-4-hydroxyphenyl)-2-(4-fluorophenylsulfonyl)acrylonitrile (741)

Example 44

(E)-3-(3,4-Dihydroxyphenyl)-2-(4-fluorophenylsulfonyl)acrylonitrile

Example 45

(E)-3-(3-Bromo-4,5-dihydroxyphenyl)-2-(4-fluorophenylsulfonyl)acrylonitrile

Example 46

(E)-3-(3-Ethoxy-4-hydroxyphenyl)-2-(4-fluorophenylsulfonyl)acrylonitrile

Example 47

(E)-3-(3,5-Dimethyl-4-hydroxyphenyl)-2-(4-fluorophenylsulfonyl)acrylonitrile

Example 48

(E)-3-(3,5-Di-t-butyl-4-hydroxyphenyl)-2-[(thien-2-yl)sulfonyl]acrylonitrile

Example 49

(E)-3-(3,5-Diisopropyl-4-hydroxyphenyl)-2-[(thien-2-yl)sulfonyl]acrylonitrile

Example 50

(E)-3-(3,4-Dihydroxyphenyl)-2-[(thien-2-yl)sulfonyl]acrylonitrile (743)

Example 51

(E)-3-(3-Bromo-4,5-dihydroxyphenyl)-2-[(thien-2-yl)sulfonyl]acrylonitrile

Example 52

(E)-3-(3-Ethoxy-4-hydroxyphenyl)-2-[(thien-2-yl)sulfonyl]acrylonitrile

Example 53

(E)-3-(3,5-Dimethyl-4-hydroxyphenyl)-2-[(thien-2-yl)sulfonyl]acrylonitrile

Example 54

(E)-3-(3,5-Di-t-butyl-4-hydroxyphenyl)-2-[(thien-3-yl)sulfonyl]acrylonitrile

Example 55

(E)-3-(3,5-Diisopropyl-4-hydroxyphenyl)-2-[(thien-3-yl)sulfonyl]acrylonitrile

Example 56

(E)-3-(3,5-Dimethyl-4-hydroxyphenyl)-2-[(thien-3-yl)sulfonyl]acrylonitrile

Example 57

(E)-3-(3,4-Dihydroxyphenyl)-2-[(thien-3-yl)sulfonyl]acrylonitrile

Example 58

(E)-3-(3-Bromo-4,5-dihydroxyphenyl)-2-[(thien-3-yl)sulfonyl]acrylonitrile

Example 59

(E)-3-(3-Ethoxy-4-hydroxyphenyl)-2-[(thien-3-yl)sulfonyl]acrylonitrile

Example 60

(E)-3-(3,5-Di-t-butyl-4-hydroxyphenyl)-2-[4-(trifluoromethyl)phenylsulfonyl]acrylonitrile

Example 61

(E)-3-(3,5-Diisopropyl-4-hydroxyphenyl)-2-[4-(trifluoromethyl)phenylsulfonyl]acrylonitrile

Example 62

(E)-3-(3,5-Dimethyl-4-hydroxyphenyl)-2-[4-(trifluoromethyl)phenylsulfonyl]acrylonitrile

Example 63

(E)-3-(3,4-Dihydroxyphenyl)-2-[4-(trifluoromethyl)phenylsulfonyl]acrylonitrile (750)

Example 64

(E)-3-(3-Bromo-4,5-dihydroxyphenyl)-2-[4-(trifluoromethyl)phenylsulfonyl]acrylonitrile

Example 65

(E)-3-(3-Ethoxy-4-hydroxyphenyl)-2-[4-(trifluoromethyl)phenylsulfonyl]acrylonitrile

Example 66

(E)-3-(3,5-Di-t-butyl-4-hydroxyphenyl)-2-[3-(trifluoromethyl)phenylsulfonyl]acrylonitrile

Example 67

(E)-3-(3,5-Dimethyl-4-hydroxyphenyl)-2-[3-(trifluoromethyl)phenylsulfonyl]acrylonitrile

Example 68

(E)-3-(3,5-Diisopropyl-4-hydroxyphenyl)-2-[3-(trifluoromethyl)phenylsulfonyl]acrylonitrile

Example 69

(E)-3-(3,4-Dihydroxyphenyl)-2-[3-(trifluoromethyl)phenylsulfonyl]acrylonitrile

Example 70

(E)-3-(3-Bromo-4,5-dihydroxyphenyl)-2-[3-(trifluoromethyl)phenylsulfonyl]acrylonitrile (751)

Example 71

(E)-3-(3-Ethoxy-4-hydroxyphenyl)-2-[3-(trifluoromethyl)phenylsulfonyl]acrylonitrile

Example 72

(E)-3-(2-Chloro-4-hydroxyphenyl)-2-[3-(trifluoromethyl)phenylsulfonyl]acrylonitrile

Example 73

(E)-3-(2-Chloro-4-hydroxyphenyl)-2-[4-(trifluoromethyl)phenylsulfonyl]acrylonitrile

Example 74

(E)-2-(Benzylaminosulfonyl)-3-(2-chloro-4-hydroxyphenyl)acrylonitrile

Example 75

(E)-3-(2-Chloro-4-hydroxyphenyl)-2-[(4-phenyl-n-butyl)aminosulfonyl]acrylonitrile

Example 76

(E)-2-Cyanomethylsulfonyl-3-(3-t-butyl-4-hydroxyphenyl)acrylonitrile

Example 77

(E,E)-2-[2-(3-t-Butyl-4-hydroxyphenyl)-1-cyanoethenylsulfonyl]-3-(3-t-butyl-4-hydroxyphenyl)acrylonitrile

Example 78

(E)-3-(3,5-Di-t-butyl-4-hydroxyphenyl)-2-(2,4-difluorophenylsulfonyl)acrylonitrile

Example 79

(E)-3-(3,5-Diisopropyl-4-hydroxyphenyl)-2-(2,4-difluorophenylsulfonyl)acrylonitrile

Example 80

(E)-3-(3,5-Dimethyl-4-hydroxyphenyl)-2-(2,4-difluorophenylsulfonyl)acrylonitrile

Example 81

(E)-3-(3,5-Di-t-butyl-4-hydroxyphenyl)-2-(4-fluorophenylsulfonyl)acrylonitrile

Example 82

(E)-2-(Benzylaminosulfonyl)-3-(3-t-butyl-4-hydroxyphenyl)acrylonitrile

Example 83

(E)-3-(3-t-Butyl-4-hydroxyphenyl)-2-[(3-phenyl-n-propyl)aminosulfonyl]acrylonitrile

Example 84

(E)-3-(3-t-Butyl-4-hydroxyphenyl)-2-(phenylsulfonyl)acrylonitrile

Example 85

(E)-3-(3-t-Butyl-4-hydroxyphenyl)-2-[(pyrid-2-yl)sulfonyl]acrylonitrile

Example 86

(E)-3-(3-t-Butyl-4-hydroxyphenyl)-2-(2,4-difluorophenylsulfonyl)acrylonitrile

Example 87

(E)-3-(3-t-Butyl-4-hydroxyphenyl)-2-(4-trifluoromethylphenylsulfonyl)acrylonitrile (752)

Example 88

(E)-3-(3-t-Butyl-4-hydroxyphenyl)-2-(3-trifluoromethylphenylsulfonyl)acrylonitrile

Example 89

(E)-2-(Benzylaminosulfonyl)-3-(3-bromo-5-t-butyl-4-hydroxyphenyl)acrylonitrile (753)

Example 90

(E)-3-(3-Bromo-5-t-butyl-4-hydroxyphenyl)-2-(4-fluorophenylsulfonyl)-acrylonitrile (754)

Example 91

(E)-3-(3-Bromo-5-t-butyl-4-hydroxyphenyl)-2-(3-trifluoromethylphenylsulfonyl)-acrylonitrile

Example 92

(E)-3-(3-Bromo-5-t-butyl-4-hydroxyphenyl)-2-(4-trifluoromethylphenylsulfonyl)-acrylonitrile

Example 93

(E)-3-(3-Bromo-5-t-butyl-4-hydroxyphenyl)-2-(2,4-difluorophenylsulfonyl)-acrylonitrile

Example 94

(E)-3-(3-Bromo-5-t-butyl-4-hydroxyphenyl)-2-[(thien-2-yl)sulfonyl]-acrylonitrile

Example 95

(E)-3-(3-Bromo-5-t-butyl-4-hydroxyphenyl)-2-[(thien-3-yl)sulfonyl]-acrylonitrile

Example 96

(E)-3-(3-Bromo-5-t-butyl-4-hydroxyphenyl)-2-[(3-phenyl-n-propyl)aminosulfonyl]acrylonitrile

Example 97

(E)-3-(3-t-Butyl-4-hydroxyphenyl)-2-[(thien-2-yl)sulfonyl]acrylonitrile

Example 98

(E)-3-(3-t-Butyl-4-hydroxyphenyl)-2-[(thien-3-yl)sulfonyl]acrylonitrile

Receptor tyrosine kinases can be used as initial test compounds to determine if one of several receptor tyrosine kinases drive the disorder. More selective compounds can then be used to further eliminate the possible role of different receptor tyrosine kinases in driving the disorder. Test compounds should be more potent in inhibiting receptor tyrosine kinase activity than in exerting a cytotoxic effect (e.g., an $IC_{50}/LD_{50}$ of greater than one). As noted above, $IC_{50}$ and $LD_{50}$ can be measured by standard techniques, such as described in the present application and using an MTT assay as described by Mossman supra, or by measuring the amount of LDH released (Korzeniewski and Callewaert, J. supra; Decker and Lohmann-Matthes, supra). The degree of $IC_{50}/LD_{50}$ of a compound should be taken into account in evaluating the diagnostic assay. Generally, the larger the ratio the more reliable the information. Appropriate controls to take into account the possible cytotoxic effect of a compound, such as treating cells not associated with a cell proliferative disorder (e.g., control cells) with a test compound, can also be used as part of the diagnostic assay.

The following examples illustrate the ability of the exemplary compounds to inhibit receptor tyrosine kinases, such as HER2 and/or EGFR. The following target cells were used for cellular kinase assays: NIH3T3 clone C7 (Honegger et al., supra) engineered to over-express human EGF receptor; NIH3T3 cells engineered to over-express a chimeric receptor containing the EGFR extracellular domain and the HER2 intracellular kinase domain; the human mammary carcinoma line BT474 (ATCC HTB2) expressing HER2; and the human glioblastoma line U1242 that expresses PDGFR-beta. Growth assays were carried out using human mammary epithelial SKBR3 (ATCC HTB30) cells (SKBR3 cells over-express HER2), SKOV3 (ATCC HTB77) human ovarian cancer cell line (SKOV3 cells also over-express HER2), A431 cells (A431 cells over-express EGFR) MCF7 human breast carcinoma cells, MCF7 cells overexpressing the HER2 kinase (MCF7-HER2), NIH3T3 cells, and NIH3T3 cells overexpressing the HER2 kinase (3T3-HER2.

The assay procedures described below were used to generate the data in the tables showing the effectiveness of the compounds of the present invention.

GROUP II ELISA TYPE ASSAYS

Example 1

EGFR Whole Cell Kinase Assay

EGFR kinase activity (EGFR-3T3 assay) in whole cells was measured as described below:

Materials & Reagents
1) EGF Ligand: stock concentration =16.5 $\mu$M; EGF 201, TOYOBO, Co., Ltd. Japan.
2) 05-101 (UBI) (a monoclonal antibody recognizing an EGFR extracellular domain).
3) Anti-Phosphotyosine antibody (polyclonal) (made according to Fendley et al., *Cancer Research* 50: 1550–1558, 1990).
4) TAGO antibody: Goat anti-rabbit IgG horse radish peroxidase conjugate, TAGO, Inc., Burlingame, Calif.
5) TBST buffer:

|  |  |
|---|---|
| Tris-HCl, pH 7.2, | 50 nM |
| NaCl, | 150 mM, |
| Triton X-100 | 0.1% |

6) HNTG 5× stock:

|  |  |
|---|---|
| HEPES | 0.1 M |
| NaCl | 0.75 M |
| Glycerol | 50% |
| Triton X-100 | 1.0% |

7) ABTS stock:

|  |  |
|---|---|
| Citric Acid | 100 mM |
| Na$_2$HPO$_4$ | 250 mM |
| HCl, conc. | 4.0 pH |
| ABTS* | 0.5 mg/ml |

*(2,2'-azinobis (3-ethylbenzthiazolinesulfonic acid). Keep solution in dark at 4° C. until use.

8) Stock reagents of:

|  |  |
|---|---|
| EDTA | 100 mM; pH 7.0 |
| Na$_3$VO$_4$ | 0.5 M |
| Na$_4$PQ | 0.2 M |

Procedure

Pre-coat ELISA Plate
A. Coat ELISA plates (Corning, 96 well, Cat. #25805-96) with 05-101 antibody at 0.5 $\mu$g per well in PBS, 150 $\mu$l final volume/well, and store overnight at 4° C. Coated plates are good for up to 10 days when stored at 4° C.
B. On day of use, remove coating buffer and replace with blocking buffer (5% Carnation Instant NonFat Dry Milk in PBS). Incubate the plate, shaking, at room temperature (about 23° C. to 25° C.) for 30 minutes. Just prior to use, remove blocking buffer and wash plate 4 times with TBST buffer.

II. Seeding Cells
A. EGFR/C7 cell line (Honegger, et al., supra) can be used for this assay.
B. Choose dishes having 80–90% confluence for the experiment. Trypsinize cells and stop reaction by adding 10% CS DMEM medium. Suspend cells in DMEM medium (10% CS DMEM medium) and centrifuge once at 1000 rpm, and once at room temperature for 5 minutes.
C. Resuspend cells in seeding medium (DMEM, 0.5% bovine serum), and count the cells using trypan blue. Viability above 90% is acceptable. Seed cells in DMEM medium (0.5% bovine serum) at a density of 10,000 cells per well, 100 $\mu$l per well, in a 96 well microtiter plate. Incubate seeded cells in 5% $CO_2$ at 37° C. for about 40 hours.

III. Assay Procedures.
A. Check seeded cells for contamination using an inverted microscope. Dilute drug stock (10 mg/ml in DMSO) 1:10 in DMEM medium, then transfer 5 $\mu$l to a test well for a final drug dilution of 1:200 and a final DMSO concentration of 1%. Control wells receive DMSO alone. Incubate in 5% $CO_2$ at 37° C. for one hour.
B. Prepare EGF ligand: dilute stock EGF in DMEM so that upon transfer of 10 $\mu$l dilute EGF (1:12 dilution), 25 nM final concentration is attained.
C. Prepare fresh HNTG* sufficient for 100 $\mu$l per well; and place on ice.

|  |  |
|---|---|
| HNTG*: | 10 ml |
| HNTG stock (5x) | 2.0 ml |
| milli-Q H$_2$O | 7.3 ml |
| EDTA, (100 mM, pH 7.0) | 0.5 ml |
| Na$_3$VO$_4$, (0.5 M) | 0.1 ml |
| Na$_4$PO$_7$, (0.2 M) | 0.1 ml |

D. After two hours incubation with drug, add prepared EGF ligand to cells, 10 $\mu$l per well, to yield a final concentration of 25 nM. Control wells receive DMEM alone. Incubate, shaking, at room temperature, for 5 minutes.
E. Remove drug, EGF, and DMEM. Wash cells twice with PBS. Transfer HNTG* to cells, 100 $\mu$l per well. Place on ice for 5 minutes. Meanwhile, remove blocking buffer from other ELISA plate and wash with TBST as described above.
F. With a pipette tip securely fitted to a micropipettor, scrape cells from plate and homogenize cell material by repeatedly aspirating and dispensing the HNTG* lysis buffer. Transfer lysate to a coated, blocked, and washed ELISA plate. Incubate shaking at room temperature for one hour.
G. Remove lysate and wash 4 times with TBST. Transfer freshly diluted anti-Ptyr antibody to ELISA plate at 100 $\mu$l per well. Incubate shaking at room temperature for 30 minutes in the presence of the anti-Ptyr antiserum (1:3000 dilution in TBST).
H. Remove the anti-Ptyr antibody and wash 4 times with TBST. Transfer the freshly diluted TAGO 30 anti-rabbit IgG antibody (anti-rabbit IgG antibody: 1:3000 dilution in TBST) to the ELISA plate at 100 $\mu$l per well. Incubate shaking at room temperature for 30 minutes.
I. Remove detection antibody and wash 4 times with TBST. Transfer freshly prepared ABTS/H$_2$O$_2$ solution to ELISA plate, 100 $\mu$l per well. Incubate at room temperature for 20 minutes. ABTS/H$_2$O$_2$ solution: 1.2 μl 30% H$_2$O$_2$ in 10 ml ABTS stock.

J. Stop reaction by adding 50 μl 5N H$_2$SO$_4$ (optional), and determine O.D. at 410 nm.

K. The maximal phosphotyrosine signal is determined by subtracting the value of the negative controls from the positive controls. The percent inhibition of phosphotyrosine content for extract-containing wells is then calculated, after subtraction of the negative controls.

Example 2

EGFR-HER2 Chimeric Recetor

HER2 kinase activity (EGFR-3T3) in whole cells was measured as described below:

Materials & Reagents

The materials and regeants are identical to these used in example 1, the EGFR whole cell kinase assay.

Procedure

I. Pre-coat ELISA Plate

A. Coat ELISA plates (Corning, 96 well, Cat. #25805-96) with 05-101 antibody at 0.5 μg per well in PBS, 100 μl final volume/well, and store overnight at 4° C. Coated plates are good for up to 10 days when stored at 4° C.

B. On day of use, remove coating buffer and replace with 100 μl blocking buffer (5% Carnation Instant Non-Fat Dry Milk in PBS). Incubate the plate, shaking, at room temperature (about 23° C. to 25° C.) for 30 minutes. Just prior to use, remove blocking buffer and wash plate 4 times with TBST buffer.

II. Seeding Cells

A. An NIH3T3 cell line overexpressing a chimeric receptor containing the EGFR extracellular domain and extracellular HER2 kinase domain can be used for this assay.

B. Choose dishes having 80–90% confluence for the experiment. Trypsinize cells and stop reaction by adding 10% fetal bovine serum. Suspend cells in DMEM medium (10% CS DMEM medium) and centrifuge once at 1500 rpm, at room temperature for 5 minutes.

C. Resuspend cells in seeding medium (DMEM, 0.5% bovine serum), and count the cells using trypan blue. Viability above 90% is acceptable. Seed cells in DMEM medium (0.5% bovine serum) at a density of 10,000 cells per well, 100 μl per well, in a 96 well microtiter plate. Incubate seeded cells in 5% CO$_2$ at 37° C. for about 40 hours.

III. Assay Procedures

A. Check seeded cells for contamination using an inverted microscope. Dilute drug stock (10 mg/ml in DMSO) 1:10 in DMEM medium, then transfer 5 l to a TBST well for a final drug dilution of 1:200 and a final DMSO concentration of 1%. Control wells receive DMSO alone. Incubate in 5% CO$_2$ at 37° C. for two hours.

B. Prepare EGF ligand: dilute stock EGF in DMEM so that upon transfer of 10 μl dilute EGF (1:12 dilution), 100 nM final concentration is attained.

C. Prepare fresh HNTG* sufficient for 100 μl per well; and place on ice.

| HNTG*: | |
|---|---|
| HNTG stock | 10 ml |
| | 2.0 ml |
| milli-Q H20 | 7.3 ml |

-continued

| EDTA, 100 mM, pH 7.0 | 0.5 ml |
|---|---|
| Na$_3$VO$_4$, (0.5 M) | 0.1 ml |
| Na$_4$PO$_7$, (0.2 M) | 0.1 ml |

D. After 120 minutes incubation with drug, add prepared SGF ligand to cells, 10 μl per well, to a final concentration of 100 nM. Control wells receive DMEM alone. Incubate, shaking, at room temperature, for 5 minutes.

E. Remove drug, EGF, and DMEM. Wash cells twice with PBS. Transfer HNTG* to cells, 100 μl per well. Place on ice for 5 minutes. Meanwhile, remove blocking buffer from other ELISA plate and wash with TBST as described above.

F. With a pipette tip securely fitted to a micropipettor, scrape cells from plate and homogenize cell material by repeatedly aspirating and dispensing the HNTG* lysis buffer. Transfer lysate to a coated, blocked, and washed ELISA plate. Incubate shaking at room temperature for one hour.

G. Remove lysate and wash 4 times with TBST. Transfer freshly diluted anti-Ptyr antibody to ELISA plate at 100 μl per well. Incubate shaking at room temperature for 30 minutes in the presence of the anti-Ptyr antiserum (1:3000 dilution in TBST).

H. Remove the anti-Ptyr antibody and wash 4 times with TBST. Transfer the freshly diluted TAGO anti-rabbit IgG antibody (anti-rabbit IgG antibody: 1:3000 dilution in TBST) to the ELISA plate at 100 μl per well. Incubate shaking at room temperature for 30 minutes.

I. Remove detection antibody and wash 4 times with TBST. Transfer freshly prepared ABTS/H$_2$O$_2$ solution (ABTS/H$_2$O$_2$ solution: 1.0 μl 30% H$_2$O$_2$ in 10 ml ABTS stock) to ELISA plate, 100 μl per well. Incubate shaking at room temperature for 20 minutes.

J. Stop reaction by adding 50 μl 5N H$_2$SO$_4$ (optional), and determine O.D. at 410 nm.

K. The maximal phosphotyrosine signal is determined by subtracting the value of the negative controls from the positive controls. The percent inhibition of phosphotyrosine content for extract-containing wells is then calculated, after subtraction of the negative controls.

Example 3

HER2-ELISA

HER2-BT474 assays measuring whole cell HER2 activity was carried out as described below:

Materials & Reagents

1. The cell line used in this assay is BT-474 (ATCC HBT20), a human breast tumor cell line which expresses high levels of HER2 kinase.

2. BT-474 is grown in an incubator with 5% CO$_2$ at 37° C. The growth media is RPMI+10% FBS+GMS-G (Gibco supplement)+Glutamine.

3. A monoclonal anti-HER2 antibody is used in ELISA.

4. D-PBS:

| KH$_2$HPO$_4$ | 0.20 g/l 10 (GIECO, 310-4190AJ) |
|---|---|
| K$_2$HPO$_4$ | 2.16 g/l |
| KCl | 0.20 g/l |
| NaCl | 8.00 g/l pH 7.2 |

5. Blocking Buffer: TBST plus 5% Milk (Carnation Instant Non-Fat Dry Milk).

6. TBST buffer:

| Tris-HCl | 50 mM pH 7.2 (HCl, 10 N) |
|---|---|
| NaCl | 150 mM |
| Triton X-100 | 0.1% |

*Stock solution of TES (10X) is prepared, and Triton X-100 is added to the buffer during dilution.

7. HNTG buffer:

| HEPES | 20 mM; pH 7.2 (HCl, 1 N) |
|---|---|
| NaCl | 150 mM |
| Glycerol | 10% |
| Triton X-100 | 0.2% |

*Stock solution (5x) is prepared and kept in 4° C.

8. EDTA-HCl: 0.5M pH 7.0 (10N HCl) as 500× stock.
9. $Na_3VO_4$: 0.5M as 100× stock is kept at −80° C. as aliquots.
10. $Na_4P_2O_7$: 0.2M as 100× stock.
11. Polyclonal antiserum anti-phosphotyrosine.
12. Goat anti-rabbit IgG, horse raddish peroxidase (POD) conjugate, Tago (Cat. No. 4520; Lot No. 1802): Tago, Inc., Burlingame, Calif.
13. ABTS solution:

| Citric acid | 100 mM |
|---|---|
| $Na_2HPO_4$ | 250 mM; pH 4.0 (1 N HCl) |
| ABTS | 0.5 mg/ml |

*ABTS: 2.2'-azinobis(3-ethylbenzthiazolinesulfonic acid)
*ABTS solution should be kept in the dark at 4° C. The solution should be discarded when it turns green.

14. Hydrogen Peroxide: 30% solution is kept in dark and 4° C.

Procedure

All the following steps are at room temperature and aseptically, performed unless stated otherwise. All ELISA plate washing is by rinsing with distilled water three times and once with TBST.

1. Cell Seeding
   (a) Grow BT474 cells in tissue culture dishes (10 cm, Corning 25020-100) to 80-90% confluence and collect using Trypsin-EDTA (0.25%, GIBCO).
   (b) Resuspend the cells in fresh medium and transfer to 96-well tissue culture plates (Corning, 25806-96) at about 25,000–50,000 cells/well (100 μl/well). Incubate the cells in 5% $CO_2$ at 37° C. overnight.
2. ELISA Plate Coating and Blocking
   (a) Coat the ELISA plate (Corning 25805-96) with anti HER2 antibody at 0.5 μg/well in 150 μl PBS overnight at 4° C., and seal with parafilm. The antibody coated plates can be used up to 2 weeks, when stored at 4° C.
   (b) On the day of use, remove the coating solution, replace with 200 μl of Blocking Buffer, shake the plate, and then remove the blocking buffer and wash the plate just before adding lysate.
3. Assay Procedures
   (a) TBST the drugs in serum-free condition. Before adding drugs, the old media is replaced with serum-free RPMI (90 μl/well)
   (b) Dilute drug stock (in 100% DMSO) 1:10 with RPMI, and transfer 10 μl/well of this solution to the cells to achieve a final drug DMSO concentration at 1%. Incubate the cells in 5% $CO_2$ at 37° C.

(c) Prepare fresh cell lysis buffer (HNTG*)

| HNTG | 2 ml |
|---|---|
| EDTA | 0.2 ml |
| $Na_3VO_4$ | 0.1 ml |
| $Na_4P_2O_7$ | 0.1 ml |
| $H_2O$ | 7.3 ml |
| HNTG* | 10 ml |

(d) After drug preincubation for two hours remove all the solution from the plate, transfer HNTG* 100 μl/well to the cells, and shake for 10 minutes.
(e) Use a 12-channel pipette to scrape the cells from the plate, and homogenize the lysate by repeat aspiration and dispensing. Transfer all the lysate to the ELISA plate and shake for 1 hour.
(f) Remove the lysate, wash the plate, add anti-pTyr (1:3,000 with TBST) 100 μl/well, and shake for 30 minutes.
(g) Remove anti-pTyr, wash the plate, add goat anti-rabbit IgG conjugated antibody (1:5,000 with TBST) 100 μl/well, and shake for 30 minutes.
(h) Remove anti-rabbit IgG antibody, wash the plate, and add fresh $ABTS/H_2O_2$ (1.2 μl 30% $H_2O_2$ to 10 ml ABTS) 100 μ/well to the plate to start color development, which usually takes 20 minutes.
(I) Measure OD 410 nM, Dynatec MR5000.

Example 4

PDGF-R Cellular Assay

The PDGF cellular kinase assay was carried out as follows: cells are lysed in 0.2M Hepes, 0.15M NaCl, 10% V/V glycerol, 0.04% Triton X-100, 5 mM EDTA, 5 rnM Na+ vanadate and 2 mM Na+ pyrophosphate; cell lysates are then added to an ELISA plate coated with an anti-PDGF receptor antibody (Genzyme); ELISA plates are coated at 0.5 μg of antibody/well in 150 μl of PBS for 18 hours at 4° C. prior to the addition of the lysate; the lysate is incubated in the coated plates for 1 hour and then washed four times in TBST (35 mM Tris-HCl pH 7.0, 0.15M NaCl, 0.1% Triton X100); anti-phosphotyrosine antibody (100 μl in PBS) is added and the mixture is incubated for 30 minutes at room temperature; the wells were then washed four times in TBST, a secondary antibody conjugated to POD (TAGO) is added to each well, and the treated well are incubated for 30 minutes at room temperature; the wells are then washed four times in TBST, $ABTS/H_2O_2$ solution is added to each well and the wells are incubated for two minutes; absorbance is then measured at 410 nm.

Example 5

Cellular IGF-1 Receptor ELISA (Version I)

U1242 MG cells were plated in 96-well plates at a concentration of $5 \times 10^4$ cells/well in cultured media containing 0.5% FBS. The cells were incubated for 24 hours. The cells were then treated with a particular compound for 2 hours followed by the addition of 100 ng/ml PDGF-BB and incubation for 10 minutes.

Cells were lysed in 0.2M Hepes, 0.15M NaCl, 10% V/V glycerol, 0.04% Triton X-100, 5 mM EDTA, 5 mM Na+ vanadate and 2 mM Na+ pyrophosphate. Cell lysates were then added to an ELISA plate coated with an anti-PDGF receptor antibody (Genzyme). ELISA plates were coated at 0.5 μg of antibody/well in 150 μl of PBS for 18 hours at 4° C. prior to the addition of the lysate.

The lysate was incubated in the coated plates for 1 hour and then washed four times in TBST (35 mM Tris-HCl pH 7.0, 0.15M NaCl, 0.1 % Triton X-100). Anti-phosphotyrosine antibody (100 μl in PBS) was added and the mixture was incubated for 30 minutes at room temperature. The wells were then washed four times in TBST, a secondary antibody conjugated to POD (TAGO) was added to each well, and the treated well were incubated for 30 minutes at room temperature. The wells were then washed four times in TBST, ABTS/$H_2O_2$ solution was added to each well and the wells were incubated for two minutes. Absorbance was then measured at 410 nm.

MATERIALS AND REAGENTS (1). The cell line used in this assay is 3T3/IGF-1R, a cell line which overexpresses IGF-1 Receptor.

(2). 3T3/IGF-1R is grown in an incubator with 5% CO2 at 37° C. The growth media is DMEM+10% FBS (heat inactivated)+2mM L-Glutamine.

(3). For ELISA plate coating, the anti-IGF-1R antibody named 17-69 is used. Antibodies are purified by the Enzymology Lab, SUGEN, Inc.

(4). D-PBS:

| | |
|---|---|
| $KH_2PO_4$ | 0.20 g/l (GIBCO 310-4190AJ) |
| $K_2HPO_4$ | 2.10 g/l |
| KCl | 0.20 g/l |
| NaCl | 8.00 g/l; pH 7.2 |

(5). Blocking Buffer: TBST plus 5% Milk (Carnation Instant Non-Fat Dry Milk)

(6). TBST buffer: Tris-HCl 50 mM NaCl 150 mM pH 7.2 (HCl, 10N) Triton X-100 0.1% *. Stock solution of TBS (10×) is prepared, and Triton X-100 is added to the buffer during dilution.

(6). HNTG buffer: HEPES 20 mM NaCl 150 mM pH 7.2 (HCl, 1N) Glycerol 10% Triton X-100 0.2 *. Stock solution (5X) is prepared and kept at 4° C.

(7). EDTA.HCl: 0.5M pH 7.0 (NaOH) as 100× stock.

(8). Na3VO4: 0.5M as 100× stock and aliquots are kept in −80° C.

(9). Na4P2O7: 0.2M as 100× stock.

(10). Insulin-like growth factor-1 from Promega (Cat# G5111).

(11). Polyclonal antiserum Anti-phosphotyrosine:

(12). Goat anti-rabbit IgG, POD conjugate (detection antibody), Tago (Cat. No. 4520; Lot No. 1802): Tago, Inc., Burlingame, Calif.

(13). ABTS solution: Citric acid 100 mM Na2HPO4 250 mM pH 4.0 (1N HCl) ABTS 0.5 mg/ml *. ABTS: 2.2'-azinobis(3-ethylbenzthiazolinesulfonic acid) *. ABTS solution should be kept in dark and 4° C. The solution should be discarded when it turns green.

(14). Hydrogen Peroxide: 30% solution is kept in the dark and at 4° C.

V. PROCEDURE

All the following steps are conducted at room temperature unless it is specifically indicated. All ELISA plate washings are performed by rinsing the plate with tap water three times, followed by one TBST rinse. Pat plate dry with paper towels.

1. Cell Seeding (1). The cells, grown in tissue culture dish (10 cm, Corning 25020-100) to 80–90% confluence, are harvested with Trypsin-EDTA (0.25%, 0.5 ml/D-100, GIBCO).

(2). Resuspend the cells in fresh DMEM +10% FBS+2 mM L-Glutamine, and transfer to 96-well tissue culture plate (Corning, 25806-96) at 20,000 cells/well (100 ul/well). Incubate for 1 day then replace medium to serum-free medium (90/ul) and incubate in 5% CO2 and 37° C. overnight.

2. ELISA Plate Coating and Blocking (1). Coat the ELISA plate (Corning 25805-96) with Anti-IGF-1R Antibody at 0.5 ug/well in 100 ul PBS at least 2 hours. (2). Remove the coating solution, and replace with 100 ul Blocking Buffer, and shake for 30 minutes. Remove the blocking buffer and wash the plate just before adding lysate.

3. Assay Procedures (1). The drugs are tested in serum-free condition.

(2). Dilute drug stock (in 100% DMSO) 1:10 with DMEM in 96-well poly-propylene plate, and transfer 10 ul/well of this solution to the cells to achieve final drug dilution 1:100, and final DMSO concentration of 1.0%. Incubate the cells in 5% CO2 at 37° C. for 2 hours.

(3). Prepare fresh cell lysis buffer (HNTG HNTG 2 ml EDTA 0.1 ml Na3VO4 0.1 ml Na4P2O7 0.1 ml H20 7.3 ml HNTG* 10 ml.

(4). After drug incubation for two hours, transfer 10 ul/well of 200nM IGF-1 Ligand in PBS to the cells (Final Conc=20 nM), and incubate at 5% CO2 at 37° C. for 10 minutes.

(5). Remove media and add 100 ul/well HNTG* and shake for 10 minutes. Look at cells under microscope to see if they are adequately lysed.

(6). Use a 12-channel pipette to scrape the cells from the plate, and homogenize the lysate by repeat aspiration and dispense. Transfer all the lysate to the antibody coated ELISA plate [V.2.(2)], and shake for 1 hour.

(7). Remove the lysate, wash the plate, transfer anti-pTyr (1:3,000 with TBST) 100 ul/well, and shake for 30 minutes.

(7). Remove anti-pTyr, wash the plate, transfer detection antibody (1:3,000 with TBST) 100 ul/well, and shake for 30 minutes.

(8). Remove detection antibody, wash the plate, and transfer fresh ABTS/H2O2 (1.2 ul H2O2 to 10 ml ABTS) 100 ul/well to the plate to start color development.

(9). Measure OD (410 nm) in Dynatec MR5000, which is connected to Ingres.

Example 6

Cellular Insulin Receptor ELISA (Version I)

The following protocol describes the cell line, reagents and procedures used to measure phosphotyrosine level on Insulin Receptor, which indicates Insulin Receptor tyrosine kinase activity.

MATERIALS AND REAGENTS (1). The cell line used in this assay is H25 (ATCC #CRL 8017), an NIH3T3 cell line which overexpresses Insulin Receptor.

(2). H25 cells are grown in an incubator with 5% $CO_2$ at 37° C. The growth media is DMEM+10% FBS (heat inactivated)+2 mM L-Glutamine.

(3). For ELISA plate coating, the monoclonal anti-IR antibody named BBE is used. Antibodies are purified by the Enzymology Lab, SUGEN, Inc.

(4). D-PBS: KH2PO4 0.20 g/l (GIBCO, 310-4190AJ) K2HPO4 2.16 g/l KCl 0.20 g/l NaCl 8.00 g/l pH 7.2.

(5). Blocking Buffer: TBST plus 5% Milk (Carnation Instant Non-Fat Dry Milk)

(6). TBST buffer: Tris-HCl 50 mM NaCl 150 mM pH 7.2 (HCl, 10N) Triton X-100 0.1% *. Stock solution of TBS (10×) is prepared, and Triton X-100 is added to the buffer during dilution.

(6). HNTG buffer: HEPES 20 mM NaCl 150 mM pH 7.2 (HCl, 1N) Glycerol 10% Triton X-100 0.2% *. Stock solution (5×) is prepared and kept at 4° C.

(7). EDTA.HCl: 0.5M pH 7.0 (NaOH) as 100× stock.

(8). Na3VO4: 0.5M as 100× stock and aliquots are kept in −80° C.

(9). Na4P2O7: 0.2M as 100× stock.

(10). Insulin from GIBCO BRL (Cat# 18125039).

(11). Polyclonal antiserum Anti-phosphotyrosine: rabbit sera generated by Enzymology Lab., SUGEN Inc.

(12). Goat anti-rabbit IgG, POD conjugate (detection antibody), Tago (Cat. No. 4520; Lot No. 1802): Tago, Inc., Burlingame, Calif.

(13). ABTS solution: Citric acid 100 mM Na2HPO4 250 mM pH 4.0 (1N HCl) ABTS 0.5 mg/ml *. ABTS: 2.2'-azinobis (3-ethylbenzthiazolinesulfonic acid) *. ABTS solution should be kept in dark and 4° C. The solution should be discarded when it turns green.

(14). Hydrogen Peroxide: 30% solution is kept in the dark and at 4° C.

IV. PROCEDURE

All the following steps are conducted at room temperature unless it is specifically indicated. All ELISA plate washings are performed by rinsing the plate with tap water three times, followed by one TBST rinse. Pat plate dry with paper towels.

1. Cell Seeding (1). The cells, grown in tissue culture dish (10 cm, Corning 25020-100) to 80–90% confluence, are harvested with Trypsin-EDTA (0.25%, 0.5 ml/D-100, GIBCO).

(2). Resuspend the cells in fresh DMEM+10% FBS+2 mM L-Glutamine, and transfer to 96-well tissue culture plate (Coming, 25806-96) at 20,000 cells/well (100 ul/well). Incubate for 1 day then replace medium to 0.01% serum medium (90/ul) and incubate in 5% CO2 and 37° C. overnight.

2. ELISA Plate Coating and Blocking (1). Coat the ELISA plate (Corning 25805-96) with Anti-IR Antibody at 0.5 ug/well in 100 ul PBS at least 2 hours.

(2). Remove the coating solution, and replace with 100 ul Blocking Buffer, and shake for 30 minutes. Remove the blocking buffer and wash the plate just before adding lysate.

3. Assay Procedures (1). The drugs are tested in serum-free condition.

(2). Dilute drug stock (in 100% DMSO) 1:10 with DMEM in 96-well poly-propylene plate, and transfer 10 ul/well of this solution to the cells to achieve final drug dilution 1:100, and final DMSO concentration of 1.0%. Incubate the cells in 5% CO2 at 37° C. for 2 hours.

(3). Prepare fresh cell lysis buffer (HNTG*) HNTG 2 ml EDTA 0.1 ml Na3VO4 0.1 ml Na4P2O7 0.1 ml H2O 7.3 ml HNTG* 10 ml.

(4). After drug incubation for two hours, transfer 10 ul/well of 1 $\mu$M Insulin in PBS to the cells (Final Conc=100 nM), and incubate at 5% CO2 at 37° C. for 10 minutes.

(5). Remove media and add 100 ul/well HNTG* and shake for 10 minutes. Look at cells under microscope to see if they are adequately lysed.

(6). Use a 12-channel pipette to scrape the cells from the plate, and homogenize the lysate by repeat aspiration and dispense. Transfer all the lysate to the antibody coated ELISA plate [V.2.(2)], and shake for 1 hour.

(7). Remove the lysate, wash the plate, transfer anti-pTyr (1:3,000 with TBST) 100 ul/well, and shake for 30 minutes.

(8). Remove anti-pTyr, wash the plate, transfer detection antibody (1:3,000 with TBST) 100 ul/well, and shake for 30 minutes.

(9). Remove detection antibody, wash the plate, and transfer fresh ABTS/H2O2 (1.2 ul H2O2 to 10 ml ABTS) 100 ul/well to the plate to start color development.

(10). Measure OD (410 nM) in Dynatec MR5000.

Example 7

ELISA Assay To Measure Kinase Activity Of FLK-I Receptor In FLK-I/NIH Cells

An ELISA assay was conducted to measure the kinase activity of the FLK-I receptor and more specifically, the inhibition or activiation of protein tyrosine kinase activity on the FLK-I receptor.

6.1. Materials And Methods

Materials. The following reagents and supplies were used:

a. Corning 96-well ELISA plates (Corning Catalog No. 25805-961;

b. Cappel Goat anti-rabbit IgG (catalog no. 55641);

c. PBS (Gibco Catalog No. 450-1300EB);

d. TBSW Buffer (50 mM Tris (pH 7.2)m 150 mM NaCl and 0.1% Tween-20);

e. Ethanolamine stock (10% ethanolamine (pH 7.0), stored at 4° C.);

f. HNTG buffer (20 mM HEPES buffer (pH 7.5), 150 mM NaCl, 0.2% Trilon X-100, and 10% Glycerol);

g. EDTA (0.5M (pH 7.0) as a 100× stock);

h. Sodium Ortho Vanadate (0.5M as a 100× stock)

i. Sodium pyro phosphate (0.2M as a 100× stock);

j. NUNC 96 well V bottom polypropylene plates (Applied Scientific Catalog No. AS-72092);

k. N1H3T3C7#3 Cells (FLK-I infected cells);

l. DMEM with IX high glucose L Gulatamine (catalog No. 11965-050);

m. FBS, Gibco (catalog no. 16000-028);

n. L-glutamine, Gibco (catalog no. 25030-016);

o. VEGF, PeproTech, Inc. (catalog no. 100-20) (kept as 1 ug/100 ul stock in Milli-Q dH$_2$O and stored at −20° C.;

p. Affinity purified anti-flk-I antiserum, Enzymology Lab, Sugen, Inc.;

q. UB40 monoclonal antibody specific for phophotyrosine, Enzymology Lab, Sugen, Inc.;

r. EIA grade Goat anti-mouse IgG-POD (BioRad catalog no. 172-1011)

S. 2,2-azino-bis(3-ethylbenz-thiazoline-6-sulfonic acid (ABTS) solution (100 mM citric acid (anhydrous), 250 mM Na$_2$HPO$_4$ (pH 4.0), 0.5 mg/ml ABTS (Sigma catalog no. A-1888)), solution should be stored in dark at 4° C. until ready for use;

t. H$_2$O$_2$ (30% solution) (Fisher catalog no. 11325);

u. ABTS/H$_2$O$_2$ (15 ml ABTS solution, 2 ul H$_2$O$_2$) prepared 5 minutes before use and left at room temperature;

v. 0.2M HCl stock in $H_2O$;
w. dimethylsulfoxide (100%) (Sigma Catalog No. D-8418); and
y. Trypsin-EDTA (Gibco BRL Catalog No. 25200-049)

Protocol. The following protocol was used to conduct the ELISA Assay:

1. Coat Corning 96-well elisa plates with 1.0 ug per well Cappel Anti-rabbit IgG antibody in 0.1M Na2CO3 pH 9.6. Bring final volume to 150 ul per well. Coat plates overnight at 4° C. Plates can be kept up to two weeks when stored at 4° C.
2. Grow cells in 30 ml of Growth media (DMEM. 2.0 mM L-Glutamine, 10% FBS) until confluent in 150 cm tissue culture dishes at 31° C., 5% $CO_2$.
3. Harvest cells by tyrpsination and seed in Corning 25850 polystyrene 96-well roundbottom cell plates, 25.000 cells/well in 200 uL of growth media.
4. Grow cells at least one day at 37° C., 5% $CO_2$.
5. Wash cells with D-PBS IX.
6. Add 200 ul/well of starvation media (DMEM, 2.0 mM 1-Glutamine, 0.1% FBS). Incubate overnight at 37° C., 5% $CO_2$.
7. Dilute Compound 1:20 in polyproplyene 96 well plates using starvation media. Dilute dimethylsulfoxide 1:20 for use in control wells.
8. Remove starvation media from 96 well cell culture plates and add 162 ul of fresh starvation media to each well.
9. Add 18 ul of 1:20 diluted Compound dilution (from step #7) to each well plus the 1:20 dimethylsulfoxide dilution to the control wells (+/− VEGF), for a final dilution of 1:200 after cell stimulation. Final dimethylsulfoxide is 0.5 %. Incubate the plate at 37° C., 5% $CO_2$ for two hours.
10. Remove unbound antibody from Elisa plates by inverting plate to remove liquid. Wash 3 times with TBSW+0.5% Ethanolamine, pH 7.0. Pat the plate on a paper towel to remove excess liquid and bubbles.
11. Block plates with TBSW+0.5% Ethanolamine, pH 7.0. 150 ul per well. Incubate plate thirty minutes while shaking on a microtiter plate shaker.
12. Wash plate 3 times as described in step 10.
13. Add 0.5 ug/well affinity purified anti-flk-I polyclonal rabbit antiserum. Bring final volume to 150 $\mu$l/well with TBSW+0.5% Ethanolamine pH 7.0. Incubate plate for thirty minutes while shaking.
14. Add 180 ml starvation medium to the cells and stimulate cells with 20 ul/well 10.0 mM Sodium Ortho Vanadate and 500 ng/ml VEGF (resulting in a final concentration of 0.1 mM Sodium Ortho Vanadate and 50 ng/ml VEGF per well) for eight minutes at 37° C., 5% $CO_2$. Negative control wells receive only starvation medium.
15. After eight minutes, media are removed from the cells and washed one time with 200 ul/well PBS.
16. Lyse cells in 150 ul/well HNTG while shaking at room temperature for five minutes. HNTG formulation includes sodium ortho vanadate, sodium pyro phosphate and EDTA.
17. Wash Elisa plate three times as described in step 10.
18. Transfer cell lysates from the cell plate to elisa plate and incubate while shaking for two hours. To transfer cell lysate pipette up and down while scrapping the wells.
19. Wash plate three times as described in step 10.
20. Incubate Elisa plate with 0.02 ug/well UB40 in TBSW+05% ethanolamine. Bring final volume to 150 ul/well. Incubate while shaking for 30 minutes.
21. Wash plate three times as described in step 10.
22. Incubate elisa plate with 1:10,000 diluted EIA grade Goat anti-mouse IgG conjugated horseradish peroxidase in TBSW+0.5% ethanolamine, pH 7.0. Bring final volume to 150 ul/well. Incubate while shaking for thirty minutes.
23. Wash plate as described in step 10.
24. Add 100 ul of ABTS/H202 solution to well. Incubate ten minutes while shaking.
25. Add 100 ul of 0.2M MCTh for 0.1M MCL final to stop the color development reaction. Shake 1 minute at room temperature. Remove bubbles with slow stream of air and read the ELISA plate in an ELISA plate reader at 410 nm.

GROUP III-IN VITRO CELL GROWTH ASSAYS

Example 8

Sulforhodamine B (SRB) Assay for Adherent Cells

Sulforhodamine B assays for measuring effects of TBST compounds on cell growth were based on procedures described by Skehan et al. J. Natl. Cancer Inst. 82:1107, 1990 incorporated herein by reference in its entirety, including any drawings. Unless otherwise stated the assays were carried out aseptically as follows:

Material & Methods (1) Sulforhodamine B Sigma Catalog S-9012 Working solution: 0.4% Sulforhodamine B=4 gram/liter 1% Acetic Acid.
(2) Trichloroacetic Acid (TCA)—Fisher Catalog #A322 Working solution: 10% TCA=100 gram TCA+1 liter $H_2O$.
(3) Acetic Acid, Glacial—Fisher Catalog A38 Working solution: 1 Acetic Acid=10 ml Acetic Acid+990 ml $H_2O$.
(4) Tris, crystallized free base—Fisher Catalog 5BP152 Working solution: 10 mM tris=1.211 gram Trizma base/liter $H_2O$.

Procedure (1) Aspirate growth media from 96 well plate containing control cells or cell treated with compounds, rinse wells 2 or 3 times with PBS and layer 200 $\mu$l cold 100 TCA onto each well. Fix cells for 60 minutes at 4° C.
(2) Discard TCA and rinse wells 5 times with distilled $H_2O$. Dry plate upside down on paper towel.
(3) Stain fixed cells for 10 minutes with 100 $\mu$l 0.4% SRB per well.
(4) Pour off SRB solution and rinse wells 5 times with 1% acetic acid.
(5) Dry plate upside down on paper towel.
(6) After wells are completely dry, solubilize dye with 100 $\mu$l 10 mM Tris base per well for 5–10 minutes on titer plate shaker.
(7) Read optical density at dual wavelength mode 570 nm and 630 nm on Dynatech ELISA plate reader, Model MR 5000.

Example 9

Soft Aqar Assay Protocol

The soft agar assay is well known in the art as a method for measuring the effects of substances on cell growth. Unless otherwise stated the soft agar assays were carried out as follows:

Material & Reagents (1) A Water bath set at 39° C. and another water bath at 37° C.
(2) 2× assay medium is comprised of 2× Dulbecco's 5Modified Eagle's Medium (DMEM) (Gibco Cat. # CA400-4ANO3) supplemented by the following:
20% Fetal Bovine Serum (FBS) 2 mM Sodium Pyruvate 4 mM Glut amine 20 mM HEPES Non-essential Amino Acids (1:50 from 100× stock)
(3) 1× assay medium made of IX DMEM supplemented with 10% FBS, 1 mM sodium pyruvate, 2 mM glutamine, 10 mM HEPES, non-essential amino acid (1:100 from 100× stock)

(4) 1.6% SeaPlaque Agarose in autoclave bottle
(5) Sterile 35 mm Corning plates (FMC Bioproducts Cat. #50102)
(6) Sterile 5 ml glass pipets (individually wrapped)
(7) Sterile 15 ml and 50 ml conical centrifuge tubes
(8) Pipets and sterile tips
(9) Sterile microcentrifuge tubes
(10) Cells in T75 flasks: SKOV-3 (ACTT HTB77)
(11) 0.25% Trypsin solution (Gibco #25200-015)

Procedure for making the base layer:

(a) Have all the media warmed up in the 37° C. water bath.

(b) To make 1× of assay medium+0.8% agar: make a 1:2 (vol:vol) dilution of melted agar (cooled to 39° C.), with 2× assay medium.

(c) Keep all media with agar warm in the 39° C. water bath when not in use.

(d) Dispense 1 ml of 1× assay medium+0.8% agar into dishes and gently swirl plate to form a uniform base layer. Bubbles should be avoided.

(e) Refrigerate base layers to solidify (about 20 minutes). Base layers can be stored overnight in the refrigerator.

Procedure for collecting cells:

(a) Take out one flask per cell line from the incubator; aspirate off medium; wash once with PBS and aspirate off; add 3 ml of trypsin solution.

(b) After all cells dissociate from the flask, add 3 ml of 1× assay media to inhibit trypsin activity. Pipet the cells up and down, then transfer the suspension into a 15 ml tube.

(c) Determine the concentration of cells using a Coulter counter, and the viability by trypan blue exclusion.

(d) Take out the appropriate volume needed to seed 3300 viable cells per plate and dilute it to 1.5 ml with 1× assay medium.

Procedure for making the upper 0.4% agarose layer:

(a) Add TBST compounds at twice the desired final assay concentration;+1.5 ml of cell suspension in 1× assay medium 10% FBS; +1.5 ml of 1× assay medium+0.8% agarose*: Total =3.0 ml IX media 10% FBS+0.4% agarose with 3300 viable cells/ml, with and without TBST compounds.

*(Made by 1:2 dilution of 2X media with 1.6% agar for the base layer procedure above.)

(b) Plate 1 ml of the Assay Mix onto the 1 ml base layer. The duplicates are plated from the 3 ml volume.

(c) Incubate the dishes for 2–3 weeks in a 100% humidified, 10% $CO_2$ incubator.

(d) Colonies that are 60 microns and larger are scored positive.

Example 10

MCF-7 SRB Growth Assay

MCF-7 cells are seeded at 2000 cells/well in a 96-well flat bottom plate in normal growth media, which was 10% FBS/RPMI supplemented with 2 mM Glutamine. The plate of cells is incubated for about 24 hours at 3° C. after which it receives an equal volume of compound dilution per well making the total volume per well 200 μl. The compound is prepared at 2 times the desired highest final concentration and serially diluted in the normal growth media in a 96-well round bottom plate and then transferred to plate of cells. DMSO serves as the vector control up to 0.2% as final concentration. The cells are then incubated at 37° C. in a humidified 5% $CO_2$ incubator.

Four days following dosing of compound, the media is discarded and 200 μ/well of ice-cold 10% TCA (Trichloroacetic Acid) is added to fix cells. After 60 minutes at 4° C., the TCA is discarded and the plate is rinsed 5 times with water. The plate is then air-dried and 100 μl/well of 0.4% SRB (Sulforhodamine B from Sigma) 20 in 1% Acetic Acid is added to stain cells for 10 minutes at room temperature. The SRB is discarded and the plate is rinsed 5 times with 1% Acetic Acid. After the plate is completely dried, 100 μl/well of 10 mM Tris-base is added to solubilize the dye. After 5 to 10 minutes, the plate is read on a Dynatech ELISA Plate Reader at dual wavelengths at 570 nm and 630 nm.

Example 11

MCF-7/HER-2 SRB Growth Assay

The protocol is basically the same as that above (for the MCF-7 Growth Assay) except that immediately before the compound is added, the normal growth media is removed and 0.5% FBS/RPMI supplemented with 2 mM Glutamine is added onto the cells. The compound is also prepared in this 0.5% serum media. The plate of cells is incubated for four days and developed as usual.

Example 12

3T3 Growth Assay

The 3T3 growth assay was carried out as follows:

Materials and Reagents
(1) Dulbecco's Modified Eagle Medium (D-MEM), Gibco 511965-050;
(2) Calf serum, Gibco 16170-029;
(3) Trypsin-EDTA, Gibco 25200-056;
(4) Fetal Bovine Serum Certified, Gibco 16000-028;
(5) Dulbecco'5 Phosphate-Buffered Saline (D-PBS), Gibco 14190-029;
(6) Sulforhodamine B (SRB), Sigma 5-9012 0.4% SRB in 1% acetic acid;
(7) 10 mM Tris-base, Fisher BP152-5;
(8) 1 0% TCA, Trichroloacetic acid, Fisher A322-500;
(9) 96-well flat bottom plate (sterile), Corning 08-757-155;
(10) 100 ml reagent reservoir 9 (sterile), Matrix Technologies Corporation, 8086;
(11) Sterile pipet tips, Fisher 21-197-8E;
(12) 50 ml sterile TBST tubes, Fisher 05-539-6.

Cell Lines
NIH3T3C7 cells in 10% CS+2 mM GLN DMEM
HER2C7 cells in 2% FBS+2 mM GLN DMEM Procedures
(1) HER2C7 (engineered to express HER2) and NIH3T3C7 (as the control) cells are used for this assay. NIH3T3C7 cells are seeded at 2500 cells/well, 10 μl/well in 10% CS+2 mM GLN DMEM, in a 96 well plate; HER2C7 cells are seeded at 6000 cells/well, 100 μl/well in 2% FBS+2 mM GLN DMEM, in a 96 well plate. Cells are incubated at 37° C., 5% $CO_2$ overnight to allow for cell attachment to the plate;

(2) The TBST compound is added to the cells at day 2. The compounds are prepared in the appropriate growth medium (10% CS+2 mM) GLN DMEM for NIH3T3C7 cells; 2% FBS+2 mM GLN DMEM for HER2C7 cells) in a 96 well plate, and serially diluted. A total of 100 μl/well medium of the diluted compounds is added into the cells. The total volume of each well is 200 μl. Quadruplicates (wells) and 11 concentration points are applied to each compound tested.

(3) After the cells are treated with the compound for 4 days, the cells are washed with PBS and fixed with 200 μl/well ice-cold 10% TCA for one hour at 0°–5° C. condition.

(4) Remove TCA and rinse wells 5 times with deionized water. Dry plates upside down with paper towels. Stain cells with 0.4% SRB at 100 μl/well for 10 minutes.

(5) Pour off SRB and rinse plate 5 times with 1 % acetic acid. Dry plate completely.

(6) Solubilize the dye with 10 mM Tris-base at 100 μl/well for 10 minutes on a shaker.

(7) Read the plate at dual wavelengths at 570 nm and 630 nm on Dynatech Elisa plate reader.

Example 13

HUV-EC—C Flk-1 assay

The HUV-EC—C Flk-1 assay can be performed as follows:

DAY 0

1. Wash and trypsinize HUV-EC-C cells (human umbilical vein endothelial cells, American Type Culture Collection; catalogue no. 1730-CRL). Wash with Dulbecco's phosphate-buffered saline (D-PBS;

obtained from Gibco BRL; catalogue no. 14190-029) 2 times at about 1 ml/10 cm$^2$ of tissue culture flask. Trypsinize with 0.05% trypsin-EDTA in non-enzymatic cell dissociation solution (Sigma Chemical Company; catalogue no. C-1544). The 0.05% trypsin was made by diluting 0.25% trypsin/1 mM EDTA (Gibco; catalogue no. 25200-049) in the cell dissociation solution. Trypsinize with about 1 ml/25–30 cm$^2$ of tissue culture flask for about 5 minutes at 37° C. After cells have detached from the flask, add an equal volume of D-PBS and transfer to a 50 ml sterile centrifuge tube (Fisher Scientific; catalogue no. 05-539-6).

2. Wash the cells with about 35 ml D-PBS in the 50 ml sterile centrifuge tube by adding the D-PBS, centrifuge for 10 minutes at approximately 200×g, aspirate the supernatant, and resuspend with 35 ml D-PBS. Repeat the wash two more times, resuspend the cells in about 1 ml assay medium/15 cm$^2$ of tissue culture flask. Assay medium consists of F12K medium (Gibco BRL; catalogue no. 21127-014)+0.5% heat-inactivated fetal bovine serum. Count the cells with a Coulter Counter$^{(R)}$(Coulter Electronics, Inc.) and add assay medium to the cells to obtain a concentration of 0.8–1.0×10$^5$ cells/ml.

3. Add cells to 96-well flat-bottom plates at 100 ul/well or 0.8–1.0×10$^4$ cells/well; incubate ~24 h at 37° C., 5% CO$_2$.

DAY 1

1. Make up two-fold drug titrations in separate 96-well plates, generally 50 uM on down to 0 uM. Use the same assay medium as mentioned in day 0, step 2 above. Titrations are made by adding 120 ul/well of drug at 200 uM (4× the final well concentration) to the top well of a particular plate column. Since the stock drug concentration is 10 mM and in 100% DMSO, the 200 uM drug concentration is 0.5% DMSO. Therefore, diluent made up of 0.5% DMSO in assay medium (F12K+0.5% fetal bovine serum) is used as diluent for the drug titrations in order to dilute the drug but keep the DMSO concentration constant. Add this diluent to the remaining wells in the column at 60 ul/well. take 60 ul from the 120 ul of 200 uM drug dilution in the top well of the column and mix with the 60 ul in the second well of the column. Take 60 ul from this well and mix with the 60 ul in the third well of the column, and so on until two-fold titrations are completed. When the next-to-the-last well is mixed, take 60 ul of the 120 ul in this well and discard it. Leave the last well with 60 ul of DMSO/media diluent as a non-drug-containing control. Make 9 columns of titrated drug, enough for triplicate wells each for 1) vascular endothelial growth factor (VEGF; obtained from Pepro Tech Inc., catalogue no. 100-20), 2) enclothelial cell growth factor (ECGF; also known as acidic fibroblast growth factor, or aFGF; obtained from Boehringer Mannheim Biochemica, catalogue no. 1439 600), and assay media control. ECGF comes as a preparation with sodium heparin.

2. Transfer 50 ul/well of the drug dilutions to the 96-well assay plates containing the 0.8–1.0×10$^4$ cells/100 ul/well of the HUV-EC-C cells from day 0 and incubate ~2 h at 37° C., 5% CO$_2$.

3. In triplicate, add 50 ul/well of 80 ug/ml VEGF, 20 ng/ml ECGF, or media control to each drug condition. As with the drugs, the growth factor concentrations are 4× the desired final concentration. Use the assay media from day 0 step 2 to make the concentrations of growth factors. Incubate ~24 h at 37° C., 5% CO$_2$. Each well will have 50 ul drug dilution, 50 ul growth factor or media, and 100 ul cells, =200 μl/well total. Thus the 4× concentrations of drugs and growth factors become 1× once everything has been added to the wells.

DAY 2

1. Add $^3$H-thymidine (Amersham; catalogue no. TRK-686) at 1 uCi/well (10 ul/well of 100 uCi/ml solution made up in RPMI media+10% heat-inactivated fetal bovine serum) and incubate ~24 h at 37° C., 5% CO$_2$. Note: $^3$H-thymidine is made up in RPMI media because all of the other applications for which we use the $^3$H-thymidine involve experiments done in RPMI. The media difference at this step is probably not significant. RPMI was obtained from Gibco BRL, catalogue no. 11875-051.

DAY 3

1. Freeze plates overnight at 20° C.

DAY 4

1. Thaw plates and harvest with a 96-well plate harvester (Tomtec Harvester 96$^{(R)}$) onto filter mats (Wallac; catalogue no. 1205-401); read counts on a Wallac Betaplate(™) liquid scintillation counter.

Example 14

IGF-1 Receptor Growth Assay

Screen III

Cell lines:

3T3/IGF-1 R (10% FBS/2 mM glutamine/DMEM)

NIH 3T3 c7 (10% calf serum/2 mM glutamine/DMEM)

NOTE: NIH 3T3 cells (and cells derived from them) should never be allowed to become confluent because this increases the chance of spontaneous transformation. If they show signs of being transformed (morphological changes, piling up, moving into clumps), throw them away and thaw a fresh batch.

Materials:

10% FBS/2 mM glutamine/DMEM 0.5% FBS/2 mM glutamine/DMEM

10% calf serum/2 mM glutamine/DMEM

IGF-1,5 μM in sterile PBS (Promega/Fisher cat. #G5111)

DMSO, tissue culture grade (Sigma cat. #D 2650)

Hits from screen II, 100 mM in DMSO 96-well plates, flat and round bottom 8 channel pipettor and sterile tips sterile reagent reservoirs sterile tubes (1.5 or 15 ml)

Methods (carry all steps out under aseptic conditions until fixing the cells for the SRB assay):

Day 0:

Cell Plating—Trypsinize and count 3T3/IGF-1R and NIH 3T3 c7 cells. Dilute in growth media to 2000 cells/200 μl and seed flat bottom 96-well plates with 200 μl/well, one plate for two compounds for each cell line.

Day 1:

Compound preparation—Add DMSO to each compound to make 100 mM stock solutions. If a compound does not go into solution with vortexing, add extra DMSO to make 50 mM or less, as required.

Aliquot each compound to 3–4 sterile screw cap tubes and store at −20° C. After thawing, make sure the compound has gone completely back into solution. Throw away after 3 freeze/thaws.

3T3/IGF-1R cells—For each 96-well plate, make 15 ml of 10 nM IGF-1/0.5% FBS/2 mM glutamine/DMEM (30 $\mu$l of 5 $\mu$M IGF-1/15 ml).

Aliquot 1.5 ml 10 nM IGF-1/0.5% FBS to a sterile tube for each compound to be tested (the first time a compound is tested, use a 15 ml tube in case it is necessary to add extra medium to get it into solution).

Add 3 $\mu$l of 100 mM stock of each compound to a tube so 200 $\mu$M final. Shake or vortex until it goes into solution. If it is necessary to add additional medium, note the final concentration.

For the DMSO control, prepare 0.5 ml/plate of 0.2% DMSO/10 nM IGF-1/0.5% FBS (2 $\mu$l DMSO/ml).

For every two compounds, aliquot 130 $\mu$l 10 nM IGF-1/0.5% FBS to wells in columns 2–11 of a 96-well round bottom plate.

Add 260 $\mu$l of each compound to four wells in column 12.

Do 2-fold dilutions (130 $\mu$l) from columns 12 to 3 on each plate (column 2 will be for the untreated control), mixing thoroughly.

Remove medium from 3T3/IGF-1 R cells, one plate at a time.

Transfer 120 $\mu$l from each well on a compound dilution plate to the corresponding well of cells.

Add 120 $\mu$l 0.2% DMSO/10 nM IGF-1/0.5% FBS to four wells in column 1.

Add 120 $\mu$l 0.5% FBS (without IGF-1) to other four wells in column 1 for negative control.

NIH 3T3 c7 cells—Carry out the same steps as for 3T3/IGF-1 R cells except use 10% calf serum instead of 0.5% FBS and do not include IGF-1.

Day 4:

Refeed—Repeat steps above, adding exactly the same IGF-1 and compound concentration to each well as before.

Day 6:

Analysis of cells—Look at wells with the highest concentrations for each compound to make sure it has not precipitated. If so, mark wells and do not use for data calculations.

Also scan plates to make sure none of the wells are contaminated. If so, mark wells and do not use for data calculations.

Detection—Follow the steps for fixing and staining described in the SOP for SRB Assays.

Whenever:

Data analysis—Find averages and standard deviations for each set of four OD's.

Using wells in column 2 (treated with IGF-1 but not compound) as 100%, calculate percent of control for each concentration of compound.

Determine the fold difference between the IGF-1-treated and untreated cells. It should be 2–3-fold.

Determine the percent of control for 0.2% DMSO. If it is less than 95%, do not use the highest compound concentration to calculate the IC$_{50}$ value.

Use a curve fit method to graph percent of control vs. log(molar concentration) and determine the IC$_{50}$.

GROUP IV—IN VIVO

Example 15

VEGF pellet model basic procedures

Theory—VEGF packaged into a time-release pellet and implanted subcutaneously on the abdomen of nude mice. This implant induces a 'reddening' response and subsequent swelling around the pellet. The objective of these studies is to implant Flk-1 inhibitors in methylcellulose near the VEGF pellet in an attempt to inhibit the 'reddening' response and subsequent swelling.

Materials—VEGF- human, recombinant, lyophilized (Peprotech, Inc., Princeton Business Park, G2; P.O. box 275, Rocky Hill, N.J. 08553)

VEGF Packaged into 21 day release pellets by Innovative Research of America, using patented matrix driven delivery system. Pellets packaged at 0.20, 0.21, or 2.1 ug VEGF/pellet. These doses approximate 10 and 100 ng/day release of VEGF. (Innovative Research of America, 3361 Executive Parkway, P.O. box 2746, Toledo, Ohio 43606)

Methylcellulose

Water (sterile)

Methanol

Appropriate drugs/inhibitors 10 cm culture plates parafilm

Methods—VEGF purchased from Peprotech and sent to Innovative Research for Custom Pellet preparation.

Methylcellulose prepared at 1.5% (w/v) in sterile water

Drugs solublized in methanol (usual concentration range= 10 to 20 mg/ml)

Place sterile parafilm in sterile 10 cm plates 150 ul of drug in methanol added to 1.35 ml of 1.5% methylcellulose and mixed/vortexed thoroughly.

25 ul aliquots of homogenate placed on parafilm and dried into discs.

Mice (6–10 wk. Balb/C athymic nu/nu, female) anesthetized via isoflurane inhalation. VEGF pellets and methylcellulose discs implanted subcutaneously on the abdomen.

Mice scored at 24 hours and 48 hours for reddening and swelling response.

Experimental Design

N=4 animals/group

Controls

VEGF pellet+drug placebo

VEGF placebo+drug pellet

The examples provided herein describe experiments that indicate the compounds of the present invention are useful in inhibiting certain in vitro activities of receptors and other signalling molecules associated with cell proliferative and cell differentiation disorders. Animal model systems can also be used to further measure the therapeutic effect of a compound. Examples of suitable animal models include subcutaneous xenograft model and in situ mammary fat pad model. Another suitable animal model described herein is the VEGF pellet model.

Example 16:

Xenoraft Model

The ability of human tumors to grow as xenografts in athymic mice (e.g., Balb/c, nu/nu) provides a useful in vivo model for studying the biological response to therapies for human tumors. Since the first successful xenotransplantation of human tumors into athymic mice by Rygaard and Povisen (Rygaard, J. and Povisen, C. O., *Acta Pathol. Microbial. Scand.*, 77:758–760, 1969.), many different human tumor cell lines (e.g., mammary, lung, genitourinary, gastrointestinal, head and neck, glioblastoma, bone, and malignant melanomas) have been transplanted and successfully grown in nude mice. Human mammary tumor cell lines, including MCF-7, ZR75-l, and MDA-MB-231, have been established as subcutaneous xenografts in nude mice (Warri, A. M., et al, *Int. J. Cancer*, 49:616–623, 1991; Ozzello, L. and Sordat, M., *Eur. J. Cancer*, 16:553–559, 1980; Osborne, C. K., et al, *Cancer* 25 Res., 45:584–590, 1985; Seibert, K., et al, *Cancer Res.*, 43:2223–2239, 1983).

To study the effect of anti-tumor drug candidates on HER2 expressing tumors, the tumor cells should be able to grow in the absence of supplemental estrogen. Many mammary cell lines are dependent on estrogen for in vivo growth in nude mice (Osborne et al., supra), however, exogenous estrogen suppresses her2 expression in nude mice (Warri et al., cupra, Dati, C., et al, *Oncogene*, 5:1001–1006, 1990). For example, in the presence of estrogen, MCF-7, ZR-75-1, and T47D cells grow well in vivo, but express very low levels of HER2 (Warri et al., supra, Dati, C., et al, *Oncogene*, 5:1001–1006).

The following type of xenograft protocol can be used: (1) implant tumor cells (subcutaneously) into the hindflank of five- to six-week-old female Balb/c nu/nu athymic mice; (2) administer the anti-tumor compound; (3) measure tumor growth by measuring tumor volume. The tumors can also be analyzed for the presence of a receptor, such as HER2, EGF or PDGF, by Western and immunohistochemical analyses. Using techniques known in the art, one skilled in the art can vary the above procedures, for example through the use of different treatment regimes.

Example 17.

Mammary Fat Pad Model

The mammary fat pad model is particularly useful for measuring the efficacy of compounds which inhibit HER2, because of the role HER2 lays in breast cancer. By implanting tumor cells directly into the location of interest, in situ models more accurately reflect the biology of tumor development than do subcutaneous models. Human mammary cell lines, including MCF-7, have been grown in the mammary fat pad of athymic mice (Shafie, S. M. and Grantham, F. H., J. Natl. Cancer Instit., 67:51–56, 1981; Goitardis, M. M., et al, J. *Steroid Biochem.*, 30:311–314, (1988). For example the following procedure can be used: (1) MDA-MB-231 and MOF-7 cells transfected with her2 are implanted at various concentrations into the auxiliary mammary fat pads of female athymic mice; (2) the compound is administered; and (3) tumor growth is measured at various time points. The tumors can also be analyzed for the presence of a receptor such as HER2, by Western and immunohistochemical analyses. Using techniques known in the art, one skilled in the art can vary the above procedures, for example through the use of different treatment regimes.

Example 18.

Toxicity

Therapeutic compounds should be more potent in inhibiting receptor tyrosine kinase activity than in exerting a cytotoxic effect. A measure of the effectiveness and cell toxicity of a compound can be obtained by determining the therapeutic index: $IC_{50}/LD_{50}$. $IC_{50}$, the dose required to achieve 50% inhibition, can be measured using standard techniques such as those described herein. $LD_{50}$ the dosage which results in 50% toxicity, can also be measured by standard techniques, such as using an MTT assay as described by Mossman J. Immunol. Methods 65:55–63 (1983), by measuring the amount of LDH released (Korzeniewski and Callewaert, *J. Immunol. Methods* 64:313 (1983); Decker and Lohmann-Matthes, *J. Immunol. Methods* 115:61 (1988), or by measuring the lethal dose in animal models. Compounds with a large therapeutic index are preferred. The therapeutic index should be greater than 2, preferably at least 10, more preferably at least 50.

In addition to measuring tumor growth to achieve a compound range which can safely be administered to a patient in the animal models, plasma half-life and biodistribution of the drug and metabolites in plasma, tumors, and major organs can be determined to facilitate the selection of drugs most appropriate for the inhibition of a disorder. Such measurements can be carried out, for example, using HPLC analysis. Compounds that show potent inhibitory activity in the screening assays, but have poor pharmacokinetic characteristics, can be optimized by altering the chemical structure and retesting. In this regard, compounds displaying good pharmacokinetic characteristics can be used as model.

Toxicity studies can also be carried out by measuring the blood cell composition. For example, toxicity studies can be carried out as follows: (1) the compound is administered to mice (an untreated control mouse should also be used); (2) blood samples are periodically obtained via the tail vein from one mouse in each treatment group; and 3) the samples are analyzed for red and white blood.

TABLE 1

| | ELISA DATA | | | | | | |
|---|---|---|---|---|---|---|---|
| Compound # | IGF-1R | IR | EGFR | PDGFR | HER2- (BT474) | HER2- (3T3) | FLK-1- (Cell.) |
| 747 | >100 | | >100 | >50 | 9.6 | >100 | >50 |
| 745 | 69 | 27 | <100 | | >50 | | |
| 731 | 29.2 | 12 | 73.2 | >50 | 0.3 | 17.2 | |
| 748 | >100 | | >100 | >100 | 5.4 | >100 | <50 |
| 732 | 11.8 | 8.8 | 58 | 50 | 1.9 | 20.9 | |
| 733 | >100 | >100 | >100 | >50 | 5.8 | 83.5 | |
| 734 | 93.9 | 51 | >100 | >50 | 1.8 | 21.7 | |
| 735 | >100 | | #100 | >100 | 0.3 | 57.4 | |
| 736 | 19 | 15.1 | 100 | >100 | 0.8 | 22.7 | |

TABLE 1-continued

ELISA DATA

| Compound # | IGF-1R | IR | EGFR | PDGFR | HER2-(BT474) | HER2-(3T3) | FLK-1-(Cell.) |
|---|---|---|---|---|---|---|---|
| 739 | >100 | | >100 | >100 | 4.1 | >100 | |
| 740 | >100 | | >100 | >100 | 0.4 | >100 | |
| 741 | 28.3 | 9.2 | 52.7 | >100 | | 13.9 | |
| 742 | >100 | | >100 | >100 | 0.2 | 27.8 | |
| 737 | 93.5 | | 77 | >100 | 1 | 32 | |
| 743 | >100 | | >100 | >100 | 12.6 | nt | |
| 744 | >100 | | >100 | >100 | 4.5 | nt | |
| 746 | >100 | | >100 | >100 | 0.3 | 8.1 | |
| 738 | >100 | | | 79.2 | >100 | 1.3 | 36.4 |

TABLE 2

Growth Data

| Compound | 3T3/IGF-1R- 0.5% FBS | 3T3/IGF-1R- 10% FBS | 3T3/HER2 2% FBS | 3T3/HER2 10% FBS | MC7/HER2 (0.5% FBS) | MCF7 10% FBS |
|---|---|---|---|---|---|---|
| 747 | nt | nt | >100 | >100 | 26 | 55 |
| 745 | nt | nt | nt | nt | nt | nt |
| 731 | 25 | 92 | 12 | 70 | 1 | 12 |
| 748 | nt | nt | >100 | >100 | 46 | >100 |
| 732 | 9.2 | 79 | 15 | 95 | 2.5 | 13 |
| 733 | nt | nt | 60 | >100 | 16 | 65 |
| 734 | nt | nt | 55 | >100 | 7 | 56 |
| 735 | nt | nt | 5 | 22 | 0.5 | 0.7 |
| 736 | 14.7 | 74 | 18 | 55 | 1 | 8 |
| 739 | nt | nt | nt | nt | 14 | 35 |
| 740 | nt | nt | 3.8 | 20 | 0.007 | 0.2 |
| 741 | 35 | 91 | 15 | 75 | 1 | 8 |
| 742 | nt | nt | 7 | 38 | 0.2 | 2 |
| 737 | nt | nt | 40 | 90 | 3 | 16 |
| 743 | nt | nt | nt | nt | nt | nt |
| 744 | nt | nt | >100 | >100 | 46 | >100 |
| 746 | nt | nt | 7 | 40 | 0.3 | 2 |
| 738 | nt | nt | 45 | >100 | 3 | 17 |

What is claimed is:

1. A compound of the formula

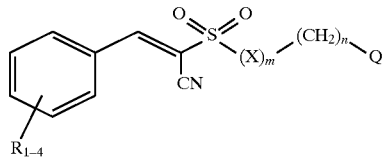

or a pharmaceutically acceptable salt thereof, wherein:

X is NH;

m is 0 or 1;

n is 0, 1, 2, 3, or 4;

Q is a phenyl ring optionally substituted with one or more substituents selected from the group consisting of halo, trihalo, alkyl, alkoxy, hydroxy, H, nitro, cyano, amide, sulfonyl, sulfonamide, carboxy, carboxamide, and amino; and $R_{1-4}$ are independently selected from the group consisting of halo, trihalo, alkyl, alkoxy, hydroxy, H, nitro, cyano, amide, sulfonyl, sulfonamide, carboxy, carboxamide, and amino;

with the proviso that when m and n are both 0, said phenyl ring is substituted.

2. The compound of claim 1, wherein m is 0.
3. The compound of claim 1, wherein m is 1.
4. The compound of claim 1, wherein n is 0.
5. The compound of claim 1, wherein n is 1.
6. The compound of claim 1, wherein n is 2.
7. The compound of claim 1, wherein n is 3.
8. The compound of claim 1, wherein n is 4.
9. A compound of the formula

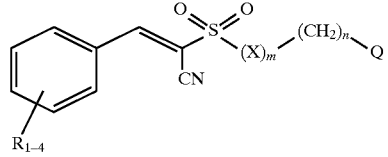

or a pharmaceutically acceptable salt thereof, wherein.

X is NH;

m is 0 or 1;

n is 1, 2, 3, or 4;

Q is a phenyl ring optionally substituted with one or more substituents selected from the group consisting of halo, trihalo, alkyl, alkoxy, hydroxy, H, nitro, cyano, amide, sulfonyl, sulfonamide, carboxy, carboxamide, and amino; and R$_{1-4}$ are independently selected from the group consisting of halo, trihalo, alkyl, alkoxy, hydroxy, H, nitro, cyano, amide, sulfonyl, sulfonamide, carboxy, carboxamide, and amino.

10. The compound of claim 1, wherein m is 0.
11. The compound of claim 1, wherein m is 1.
12. The compound of claim 1, wherein n is 1.
13. A compound selected from the group consisting of:
(E)-3-(3,5-Dimethyl4-hydroxyphenyl)-2-(phenylsulfonyl)acrylonitrile,
(E)-3-(3,5-Di -t-butyl-4-hydroxyphenyl)-2-(phenylsulfonyl)acrylonitrile,
(E)-2-(Benzylaminosulfonyl)-3-(3,5-di-t-butyl4-hydroxyphenyl)acrylonitrile,
(E)-2-(Benzylaminosulfonyl)-3-(3,5-diisopropyl-4-hydroxyphenyl)acrylonitrile,
(E)-2-(Benzylaminosulfonyl)-3-(3,5-dimethyl-4-hydroxyphenyl)acrylonitrile,
(E)-3-(3,5-Di-t-butyl-4-hydroxyphenyl)-2-[(3-phenyl-n-propyl)aminosulfonyl]acrylonitrile,
(E)-3-(3,5-Diisopropyl-4-hydroxyphenyl)-2-[(3-phenyl)-n-propyl)aminosulfonyl]acrylonitrile),
(E)-3-(3,5-Dimethyl-4-hydroxyphenyl)-2-[(3-phenyl-n-propyl)aminosulfonyl]acrylonitrile,
(E)-3-(3-t-Butyl-4-hydroxyphenyl)-2-(4-fluorophenylsulfonyl)acrylonitrile,
(E)-3-(3-Bromo4,5-dihydroxyphenyl)-2-(phenylsulfonyl)acrylonitrile,
(E)-3-(3,4-Dihydroxyphenyl)-2-(phenylsulfonyl)acrylonitrile,
(E)-2-(Benzylaminosulfonyl)-3-(3,4-dihydroxyphenyl)acrylonitrile,
(E)-2-(Benzylaminosulfonyl)-3-(4-hydroxy-3-ethoxyphenyl)acrylonitrile,
(E)-2-(Benzylaminosulfonyl)-3-(3-bromo-4,5-dihydroxyphenyl)acrylonitrile,
(E)-3-(3-Bromo-4,5-dihydroxyphenyl)-2-[(4-phenyl-n-butyl)aminosulfonyl]acrylonitrile,
(E)-3-(3-Ethoxy-4-hydroxyphenyl)-2-[(3-phenyl-n-propyl)aminosulfonyl]acrylonitrile,
(E)-3-(3,4-Dihydroxyphenyl)-2-[(3-phenyl-n-propyl)aminosulfonyl]acrylonitrile,
(E)-3-(4-Hydroxy-3-ethoxyphenyl)-2-(phenylsulfonyl)acrylonitrile,
(E) -3-(3,5-Di-t-butyl4-hydroxyphenyl)-2-[3-(trifluoromethyl)benzylsulfonyl]acrylonitrile,
(E)-3-(3,5-Diisopropyl-4-hydroxyphenyl)-2-[3-(trifluoromethyl)benzylsulfonyl]acrylonitrile,
(E)-3-(3-Ethoxy-4-hydroxyphenyl)-2-[(3-trifluoromethyl)benzylsulfonyl]acrylonitrile,
(E)-3-(3-Bromo-4,5-dihydroxyphenyl)-2-[3-(trifluoromethyl)benzylsulfonyl]acrylonitrile,
(E)-3-(3,5-Dimethyl-4-hydroxyphenyl)-2-[3-(trifluoromethyl)benzylsulfonyl]acrylonitrile,
(E)-3-(3,4-Dihydroxyphenyl)-2-[3-(trifluoromethyl)benzylsulfonyl]acrylonitrile,
(E)-2-(4-Fluorophenylsulfonyl)-3-(4-hydroxy-3,5-di-t-butylphenyl)acrylonitrile,
(E)-3-(3,5-Diisopropyl-4-hydroxyphenyl)-2-(4-fluorophenylsulfonyl)acrylonitrile,
(E)-3-(3,4-Dihydroxyphenyl)-2-(4-fluorophenylsulfonyl)acrylonitrile,
(E)-3-(3-Bromo-4,5-dihydroxyphenyl)-2-(4-fluorophenylsulfonyl)acrylonitrile,
(E)-3-(3-Ethoxy-4-hydroxyphenyl)-2-(4-fluorophenylsulfonyl)acrylonitrile,
(E)-3-(3,5-Dimethyl-4-hydroxyphenyl)-2-(4-fluorophenylsulfonyl)acrylonitrile,
(E)-3-(3,5-Di-t-butyl4-hydroxyphenyl)-2-[4-(trifluoromethyl)phenylsulfonyl]acrylonitrile,
(E)-3-(3,5-Diisopropyl-4hydroxyphenyl)-2-[4-(trifluoromethyl)phenylsulfonyl]acrylonitrile,
(E)-3-(3,5-Dimethyl4-hydroxyphenyl)-2-[4(trifluoromethyl)phenylsulfonyl]acrylonitrile,
(E)-3-(3,4-Dihydroxyphenyl)-2-[4-(trifluoromethyl)phenylsulfonyl]acrylonitrile,
(E)-3-(3-Bromo-4,5-dihydroxyphenyl)-2-[4-(trifluoromethyl)phenylsulfonyl]acrylonitrile,
(E)-3-(3-Ethoxy-4-hydroxyphenyl)-2-[4-(trifluoromethyl)phenylsulfonyl]acrylonitrile,
(E)-3-(3,5-Di-t-butyl-4-hydroxyphenyl)-2-[3-(trifluoromethyl)phenylsulfonyl]acrylonitrile,
(E)-3-(3,5-Dimethyl-4-hydroxyphenyl)-2-[3-(trifluoromethyl)phenylsulfonyl]acrylonitrile,
(E) -3-(3,5-Diisopropyl-4-hydroxyphenyl)-2-[3-(trifluoromethyl)phenylsulfonyl]acrylonitrile,
(E)-3-(3,4Dihydroxyphenyl)-2-[3-(trifluoromethyl)phenylsulfonyl]acrylonitrile,
(E)-3-(3-Bromo-4,5-dihydroxyphenyl)-2-[3-(trifluoromethyl)phenylsulfonyl]acrylonitrile,
(E)-3-(3-Ethoxy4-hydroxyphenyl)-2-[3-(trifluoromethyl)phenylsulfonyl]acrylonitrile,
(E)-3-(2-Chloro-4-hydroxyphenyl)-2-[3-(trifluoromethyl)phenylsulfonyl]acrylonitrile,
(E)-3-(2-Chloro-4-hydroxyphenyl)-2-[4-(trifluoromethyl)phenylsulfonyl]acrylonitrile,
(E)-2-(Benzylaminosulfonyl)-3-(2-chloro-4-hydroxyphenyl)acrylonitrile,
(E)-3-(2-Chloro-4-hydroxyphenyl)-2-[(4-phenyl-n-butyl)aminosulfonyl]acrylonitrile,
(E)-3-(3,5-Di-t-butyl-4-hydroxyphenyl)-2-(2,4-difluorophenylsulfonyl)acrylonitrile,
(E)-3-(3,5-Diisopropyl4-hydroxyphenyl)-2-(2,4-difluorophenylsulfonyl)acrylonitrile,
(E)-3-(3,5-Dimethyl-4-hydroxyphenyl)-2-(2,4-difluorophenylsulfonyl)acrylonitrile,
(E)-3-(3,5-Di-t-butyl4-hydroxyphenyl)-2-(4-fluorophenylsulfonyl)acrylonitrile,
(E)-2-(Benzylaminosulfonyl)-3-(3-t-butyl-4-hydroxyphenyl)acrylonitrile,
(E)-3-(3-t-Butyl-4-hydroxyphenyl)-2-[(3-phenyl-n-propyl)aminosulfonyl]acrylonitrile,
(E)-3-(3-t-Butyl-4-hydroxyphenyl)-2-(phenylsulfonyl)acrylonitrile,
(E)-3-(3-t-Butyl -4-hydroxyphenyl)-2-(2,4-difluorophenylsulfonyl)acrylonitrile,
(E)-3-(3-t-Butyl-4-hydroxyphenyl)-2-(4-trifluoromethylphenyl sulfonyl)acrylonitrile,
(E)-3-(3-t-Butyl -4-hydroxyphenyl)-2-(3-trifluoromethylphenyl sulfonyl)acrylonitrile,
(E)-2-(Benzylaminosulfonyl)-3-(3-bromo-5-t-butyl-4-hydroxyphenyl)acrylonitrile,
(E)-3-(3-Bromo-5-t-butyl-4-hydroxyphenyl)-2-(4-fluorophenylsulfonyl)-acrylonitrile, (E)-3-(3-Bromo-5-t-butyl-4-hydroxyphenyl)-2-(3-trifluoromethylphenylsulfonyl)-acrylonitrile, (E)-3-(3-Bromo-5-t-butyl-4-hydroxyphenyl) -2-(4-trifluoromethylphenylsulfonyl)-acrylonitrile, (E)-3-(3-Bromo-5-t-butyl-4-hydroxyphenyl)-2-(2,4-difluorophenylsulfonyl)-acrylonitrile, and (E)-3-(3-Bromo-5-t-butyl-4-hydroxyphenyl)-2-[(3-phenyl-n-propyl)aminosulfonyl]acrylonitrile; or a pharmaceutically acceptable salt of said compound.

14. The compound of claim 13, wherein said compound selected from the group consisting of (E)-2-(B3 enzylaminosulfonyl)-3-(3,5-diisopropyl4-hydroxyphenyl)acrylonitrile, (E)-2-(Benzylaminosulfonyl)-3-(2-chloro-4-hydroxyphenyl)acrylonitrile, (E)-3-(2-Chloro-4-hydroxyphenyl)-2-[(3-phenyl-n-propyl)aminosulfonyl]acrylonitrile, (E)-3-(3,5-Di-t-butyl-4-hydroxyphenyl)-2-[3-(trifluoromethyl)benzylsulfonyl]acrylonitrile, (E)-3-(3,5-Diisopropyl-4-hydroxyphenyl)-2-[3 (trifluoromethyl)benzylsulfonyl]acrylonitrile, (E)-3-(3,5-Dimethyl-4-hydroxyphenyl)-2-[3-(trifluoromethyl)benzylsulfonyl]acrylonitrile, (E)-3-(3,5-Di-t-butyl-4-hydroxyphenyl)-2-(4-fluorophenylsulfonyl)acrylonitrile, (E)-3-(3,5-Diisopropyl-4-hydroxyphenyl)-2-(4-fluorophenylsulfonyl)acrylonitrile, (E)-3-(3,5-Dimethyl -4-hydroxyphenyl)-2-(4-fluorophenylsulfonyl)acrylonitrile, (E)-3-(3,5-Dimethyl4-hydroxyphenyl)-2-(phenylsulfonyl)acrylonitrile, (E)-3-(3,4-Dihydroxyphenyl)-2-[4-(trifluoromethyl)phenylsulfonyl]acrylonitrile, and (E)-3-(3-Bromo-5-t-butyl-4-hydroxyphenyl)-2-(4-fluorophenylsulfonyl)-acrylonitrile.

15. The compound of claim 13, wherein said compound is (E)-3-(3,5-Diisopropyl-4-hydroxyphenyl)-2-[3 (trifluoromethyl)benzylsulfonyl]acrylonitrile, or a pharmaceutically acceptable salt thereof.

16. A pharmaceutical composition, comprising an effective amount of a compound of any one of claims 1–15, or a pharmaceutically acceptable salt of said compound, and a pharmaceutically acceptable carrier or diluent.

* * * * *

UNITED STATES PATENT AND TRADEMARK OFFICE
CERTIFICATE OF CORRECTION

PATENT NO. : 5,891,917
DATED : April 6, 1999
INVENTOR(S) : Peng Cho Tang, et. al.

It is certified that error appears in the above-identified patent and that said Letters Patent is hereby corrected as shown below:

Column 51, Line 12: delete "(E)-2-(B3 enzylaminosulfonyl)-3-(3,5-diisopropyl-4-hydroxyphenyl)acrylonitrile" and insert --(E)-2-(Benzylaminosulfonyl)-3-(3,5-diisopropyl-4-hydroxyphenyl)acrylonitrile--

Signed and Sealed this

Thirtieth Day of November, 1999

Attest:

Q. TODD DICKINSON

*Attesting Officer*   *Acting Commissioner of Patents and Trademarks*